(12) United States Patent
Jian et al.

(10) Patent No.: US 12,379,586 B2
(45) Date of Patent: Aug. 5, 2025

(54) TECHNIQUES FOR SENSORLESS ADAPTIVE OPTICS OPTICAL COHERENCE TOMOGRAPHY

(71) Applicant: Oregon Health & Science University, Portland, OR (US)

(72) Inventors: Yifan Jian, Portland, OR (US); Acner Camino Benech, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 741 days.

(21) Appl. No.: 17/689,048

(22) Filed: Mar. 8, 2022

(65) Prior Publication Data

US 2022/0299753 A1 Sep. 22, 2022

Related U.S. Application Data

(60) Provisional application No. 63/158,207, filed on Mar. 8, 2021.

(51) Int. Cl.
| | |
|---|---|
| G02B 26/08 | (2006.01) |
| A61B 3/10 | (2006.01) |
| A61B 3/12 | (2006.01) |
| A61B 3/14 | (2006.01) |

(52) U.S. Cl.
CPC .......... *G02B 26/0825* (2013.01); *A61B 3/102* (2013.01); *A61B 3/1241* (2013.01); *A61B 3/14* (2013.01)

(58) Field of Classification Search
CPC ... G02B 26/0825; A61B 3/102; A61B 3/1241; A61B 3/14; A61B 3/1233
See application file for complete search history.

(56) References Cited

U.S. PATENT DOCUMENTS

| | | | | |
|---|---|---|---|---|
| 2020/0258295 | A1* | 8/2020 | Hirokawa | ............ A61B 3/0025 |
| 2024/0065544 | A1* | 2/2024 | Jia | .......................... A61B 3/102 |

* cited by examiner

*Primary Examiner* — James C. Jones
(74) *Attorney, Agent, or Firm* — Schwabe, Williamson & Wyatt, P.C.

(57) ABSTRACT

Disclosed are methods and systems for adaptive optics (AO)-optical coherence tomography (OCT) and OCT angiography (OCTA). Embodiments include techniques to generate one or more volumetric and/or depth-resolved figures of merit to guide optimization of ocular aberrations in sensorless AO-OCT and/or AO-OCTA. The one or more figures of merit may be generated in real-time, e.g., in parallel with the OCT scan and/or aberration optimization process. Other embodiments may be described and claimed.

12 Claims, 16 Drawing Sheets
(15 of 16 Drawing Sheet(s) Filed in Color)

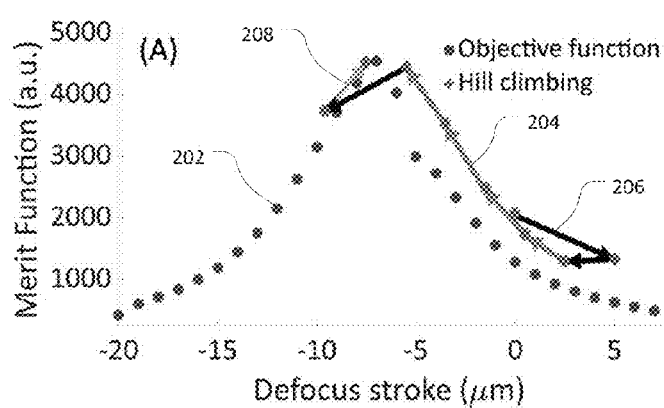
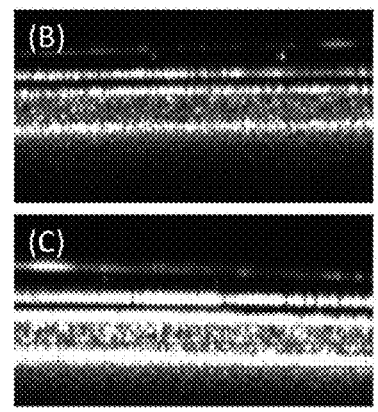
Figure 2A
Figure 2B
Figure 2C

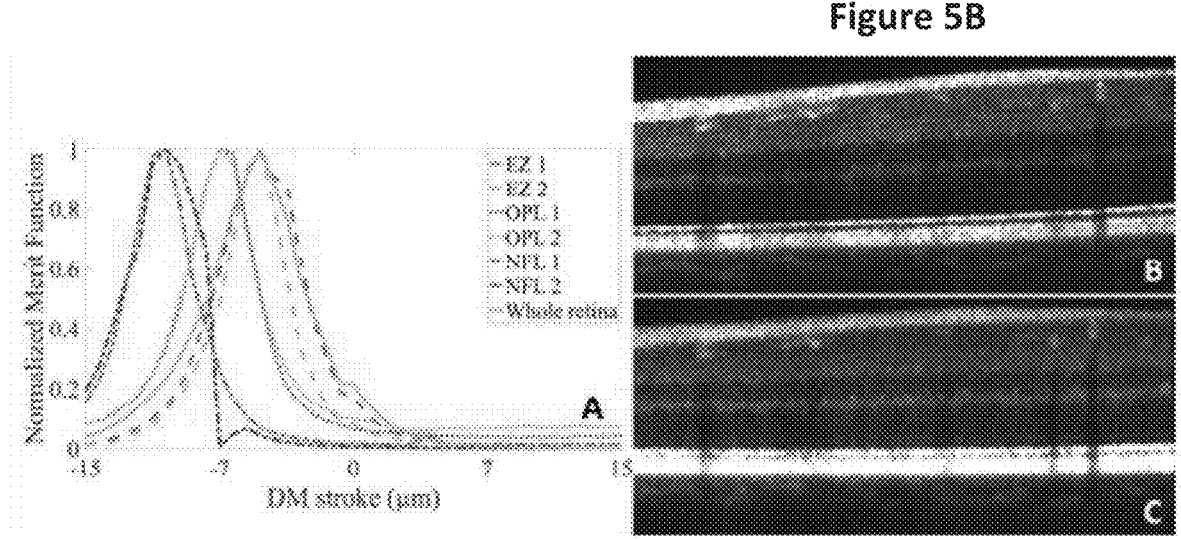
Figure 5A  Figure 5B  Figure 5C
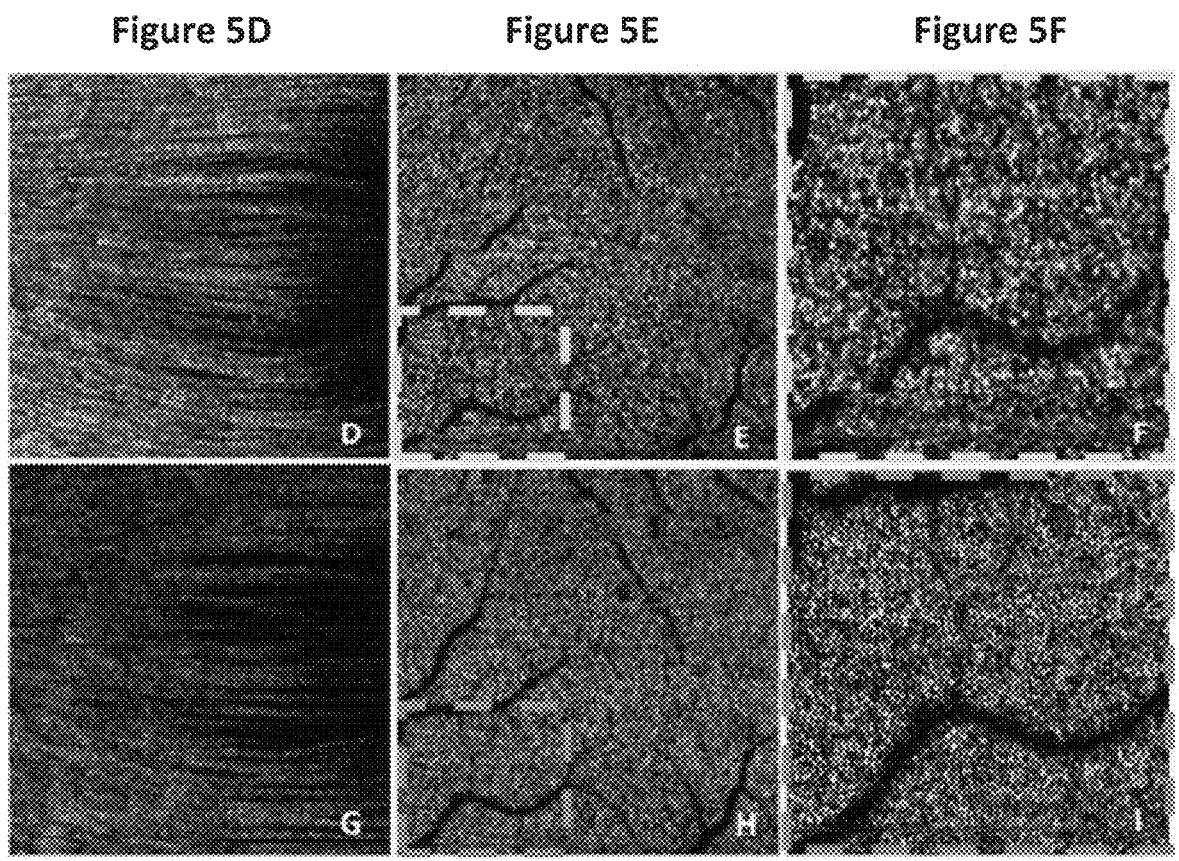
Figure 5D  Figure 5E  Figure 5F
Figure 5G  Figure 5H  Figure 5I Figure 6A
Figure 6B
Figure 6C
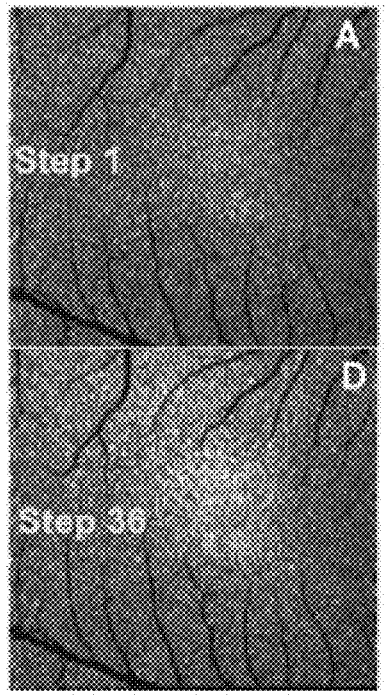
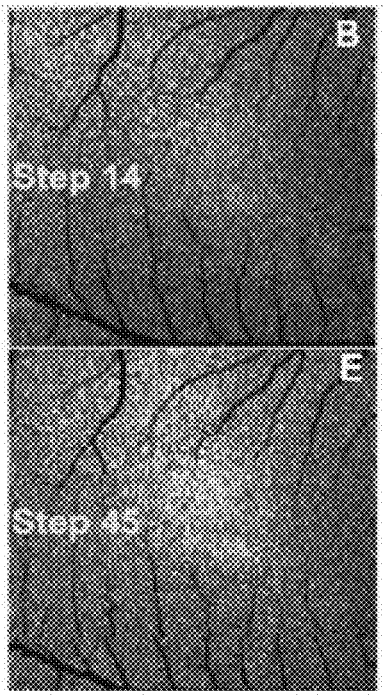
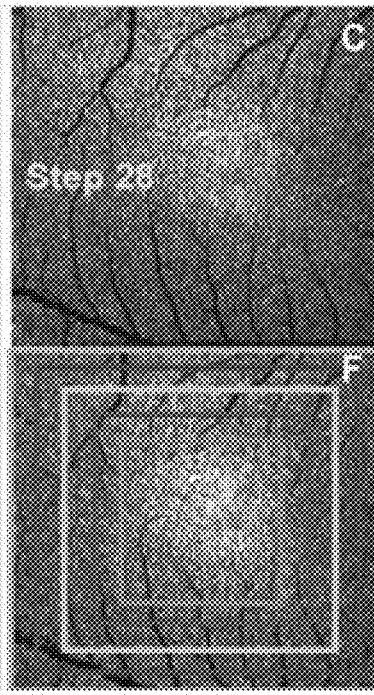
Figure 6D
Figure 6E
Figure 6F
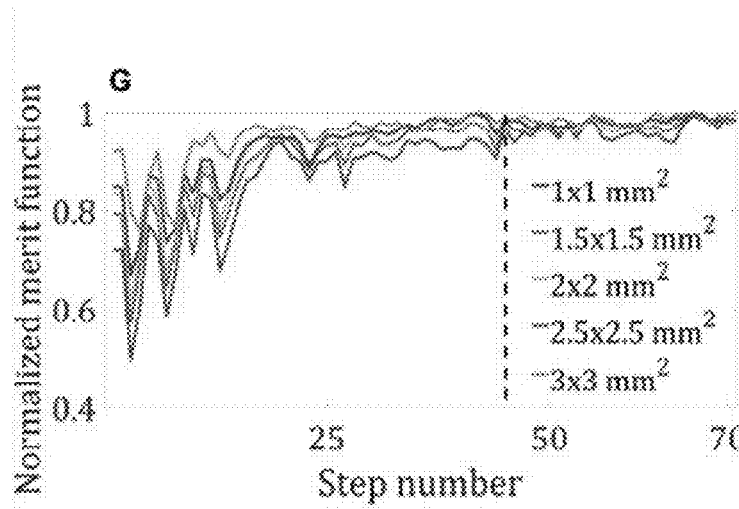
| Window outer boundary | Cross-correlation |
|---|---|
| 1.25 x 1.25 | 0.9829 |
| 1.5 x 1.5 | 0.9915 |
| 1.75 x 1.75 | 0.981 |
| 2 x 2 | 0.9739 |
| 2.25 x 2.25 | 0.9649 |
| 2.5 x 2.5 | 0.9517 |
| 2.75 x 2.75 | 0.9213 |
| 3 x 3 | 0.8449 |
Figure 6G Figure 12A
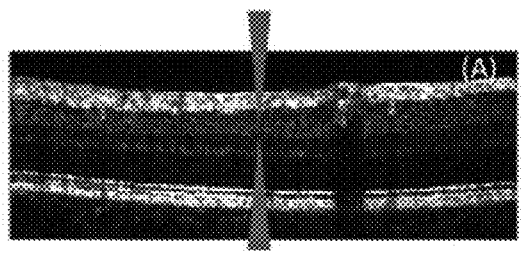
Figure 12B
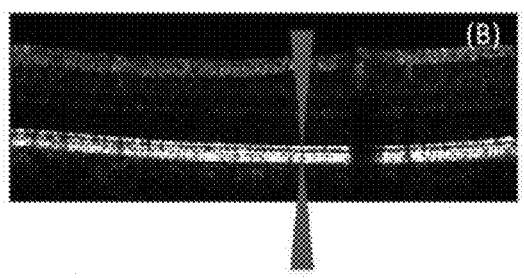
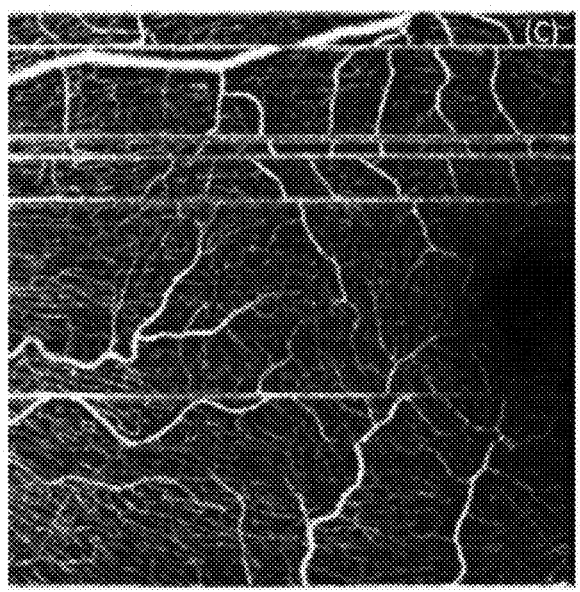
Figure 12C
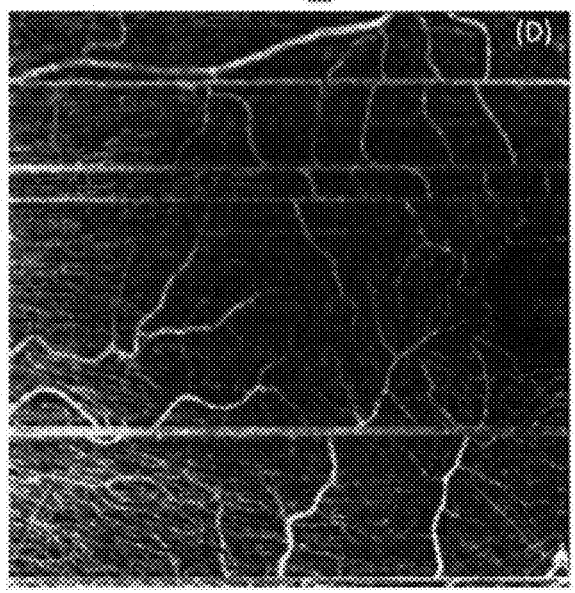
Figure 12D

TECHNIQUES FOR SENSORLESS ADAPTIVE OPTICS OPTICAL COHERENCE TOMOGRAPHY

CROSS REFERENCE TO RELATED APPLICATION

This application claims priority to U.S. Provisional Patent Application No. 63/158,207, filed Mar. 8, 2021, which is hereby incorporated by reference in its entirety.

ACKNOWLEDGEMENT OF GOVERNMENT SUPPORT

This invention was made with government support under P30 EY010572 awarded by the National Institutes of Health. The government has certain rights in the invention.

STATEMENT REGARDING COLOR DRAWINGS/PHOTOGRAPHS

The patent or application file contains a least one drawing/photograph executed in color. Copies of this patent or patent application publication with color drawing(s)/photograph(s) will be provided by the Office upon request and payment of the necessary fee.

FIELD

Generally, the field involves imaging using optical coherence tomography. In particular, the field involves sensorless adaptive optics (AO)-optical coherence tomography (OCT) and OCT angiography (OCTA).

BACKGROUND

Adaptive optics (AO) optical coherence tomography (OCT) and OCT angiography (OCTA) is a technology to achieve high lateral resolution imaging of the retinal tissue and flow by compensating for ocular aberrations. However, the use of AO-OCT and AO-OCTA in a clinic setting has been challenged by a number of factors including large instrument footprint, high cost, narrow FOV and limited depth of focus. In addition, AO-OCT has historically required long imaging sessions and very cooperative subjects. Furthermore, wavefront sensors used to measure the optical aberrations of the eye increase the cost and footprint of the instrument, reduce the optical efficiency of the sample arm, and their accuracy is vulnerable to specular reflections from the lenses commonly used in an OCT sample arm.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

FIG. 2A-2C illustrate the performance of the aberration optimization method, such as the method of FIG. 1, in accordance with various embodiments. FIG. 2A illustrates a coordinate search (dark blue dots 202) characterizing the objective function of defocus in a model eye by iterating through the entire dynamic range of the deformable mirror. Hill climbing starting from zero stroke converged close to the maximum value of merit function within nine iterations. Light blue arrows 204 and black arrows 206 represent positive and negative gradients of the merit function respectively. The green arrow 208 indicates that the parabolic fit was triggered, reaching the maximum of the objective function at a peak-to-valley stroke=−7 μm. FIG. 2B illustrates OCT reflectance before optimization, and FIG. 2C illustrates the OCT reflectance after the hill climbing process was applied.

FIGS. 5A-5I illustrate the effect of axial tracking on optimization of ocular aberrations of a healthy eye by a sensorless AO-OCT prototype, in accordance with various embodiments. The depth of focus in AO-OCT is not sufficient to maintain the whole retina on focus. FIG. 5A illustrates a coordinate search analysis of the deformable mirror stroke necessary to achieve focus control at three different retinal depths (e.g., nerve fiber layer (NFL), outer plexiform layer (OPL), and ellipsoid zone (EZ)). Optimization without axial tracking (whole retina) conduced to biased optimization of the EZ, which would be detrimental for visualization of inner retinal structures. FIGS. 5B and 5D-5F are examples of hill climbing optimization of the five Zernike modes in FIG. 4 for the NFL and EZ respectively. FIGS. 5C and 5G-5I are examples of hill climbing optimization of the five Zernike modes in FIG. 4 for the EZ. The field of view (FOV) is 4.5 degrees. FIGS. 5F and 5I are the areas marked in FIGS. 5E and 5H, respectively, covering a 2-degree FOV, zoomed in for improved visualization of the photoreceptor mosaic. FIGS. 5D-5F show optimization for NFL depth with defocused EZ while FIGS. 5G-5I show optimization for EZ depth with defocused NFL.

FIGS. 6A-6G illustrate a method to determine the maximum FOV recommended in a sensorless AO-OCT instrument. FIG. 6A-6E illustrate evolution of en face reflectance projections of a 3×3 mm area scanned in high-speed mode. FIG. 6F illustrates division of sub-FOVs marked in the colored scheme represented in FIG. 6G. The dashed line in FIG. 6G represents the end of the optimization routine. To assess stability 27 additional merit functions were acquired without modifying the deformable mirror configuration. Merit functions were computed for each digitally cropped sub-FOV in FIG. 6F, excluding the pixels contained in the largest inscribed sub-FOV and normalized to each of their maximum values. The signals of the rectangular sections of arbitrary size were then cross-correlated with the signal of the central 1×1 $mm^2$. As observed in the table, the cross-correlation of the merit function of the central square with the merit functions of the rectangular sections between 2.5×2.5 mm² and the 3×3 mm² squares were lower than 0.95. A maximum FOV of about 2.5×2.5 mm² would be acquired.

FIG. 7A shows the CAD design done in SolidWorks and FIG. 7B shows a picture of the sample arm on a 12"×12" breadboard. A fiber coupler (90%-10%, Gould Fiber Optics) directs the light from the superluminescent diode (M-D-840-HP, Superlum) through a reflective collimator into the sample arm shown in FIG. 7A. The components labeled in FIG. 7A are: C—Reflective collimator (Thorlabs, Inc.) M1-M4—Mirrors. L1-L4—Lenses with focal length of 150 mm, 60 mm, 100 mm and 75 mm respectively. GS—Galvo scanner (Cambridge Technologies). DM—Deformable mirror (DM69, ALPAO, Inc.). Dic M—Dichroic mirror redirecting visible light to an upper level with the fixation target. A spectrometer (Cobra-S 800, Wasatch photonics) with a 2048-pixel camera (Octoplus, Teledyne e2v) was used to read the OCT interferograms. Optical fiber patches were added to the sample and reference arms to compensate delay and dispersion. A dummy mirror was placed at the position of the deformable mirror in the picture for alignment purposes. Spacers were 3D printed. The sample arm efficiency was 75%.

FIG. 8A illustrates a ray trace simulation. FIG. 8B illustrates a simulation of the beam size (≈6 μm) over a field of view of 4.5 mm centered at the fovea of an emmetropic eye model.

FIGS. 12A-12D illustrate layer-specific optimization of focusing using sensor-less AO with real-time image processing segmentation of retinal layers. FIG. 12A illustrates focusing with a figure of merit based on the inner retina layers produces a cross-sectional OCT image with bright inner layers. FIG. 12B illustrates a figure of merit based on the entire B-frame to bring the focus to the outer retina with its highly backscattering ellipsoid zone—retinal pigment epithelium complex. FIG. 12C illustrates focusing on the inner retina optimizes the sharpness of retinal OCTA. FIG. 12D illustrates focusing on the outer retina blurs the retinal OCTA. Field of view is 3.3×3.3 mm.

DETAILED DESCRIPTION

Figure 1:
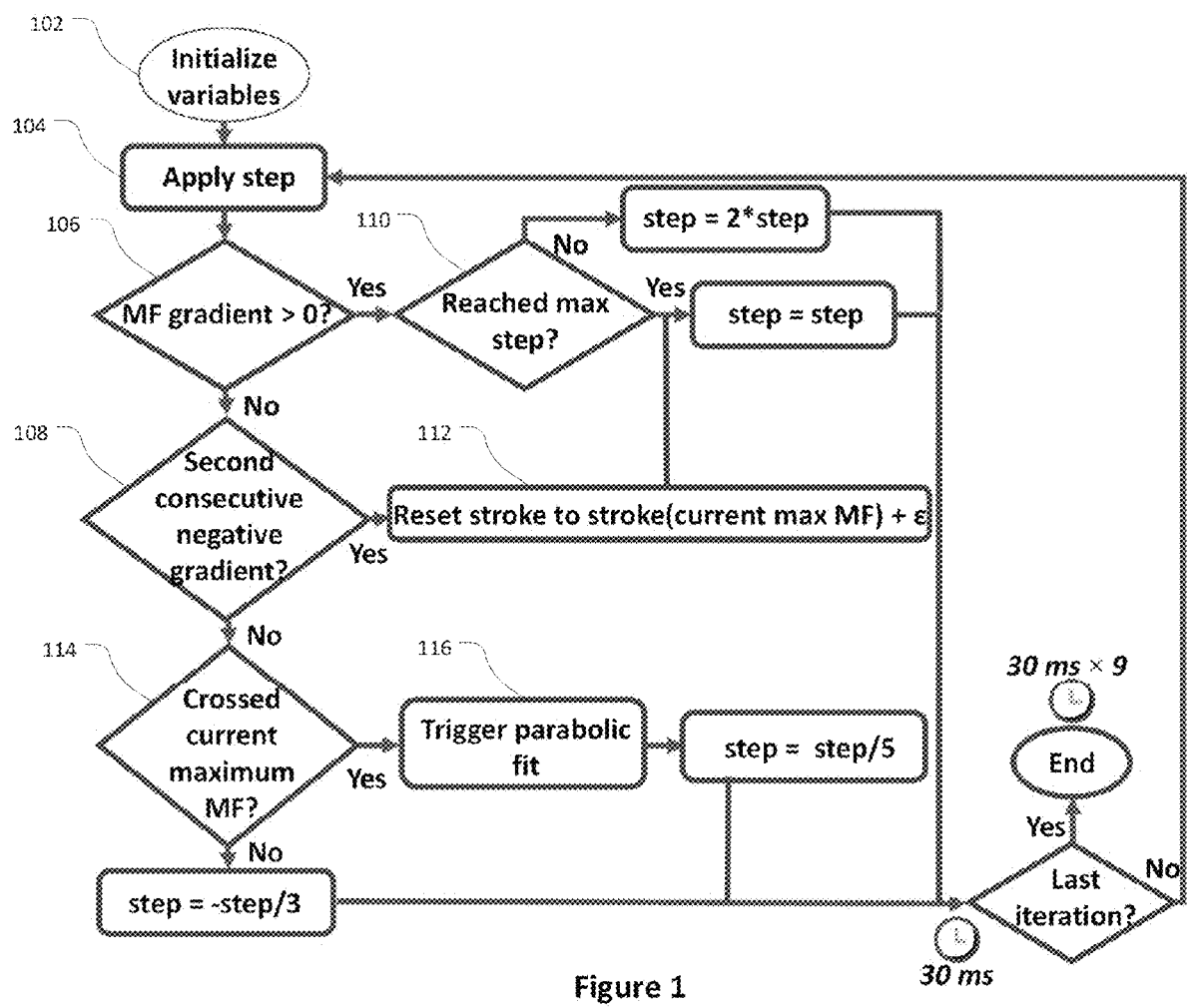
FIG. 1 illustrates a method (e.g., hill-climbing method) for aberration optimization for AO-OCT, in accordance with various embodiments.
Figure 3A:
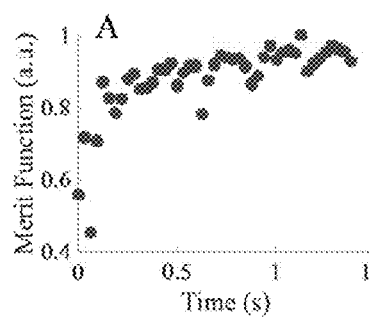
FIGS. 3A-3D illustrate adaptive-step hill climbing optimization of a merit function based on the reflectance of depth-tracked outer plexiform layer (FIGS. 3A-3B) and ellipsoid zone (FIGS. 3C-3D) at an eccentricity of 5 degrees superior to the fovea.
Figure 3C:
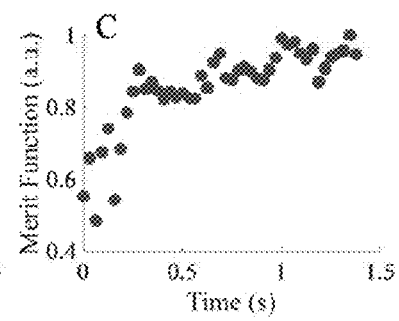
Figure 3E:
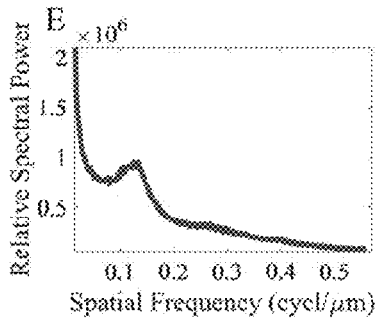
FIG. 3E illustrates Yellot's ring peak corresponding to photoreceptors in FIG. 3D.
Figure 3B:
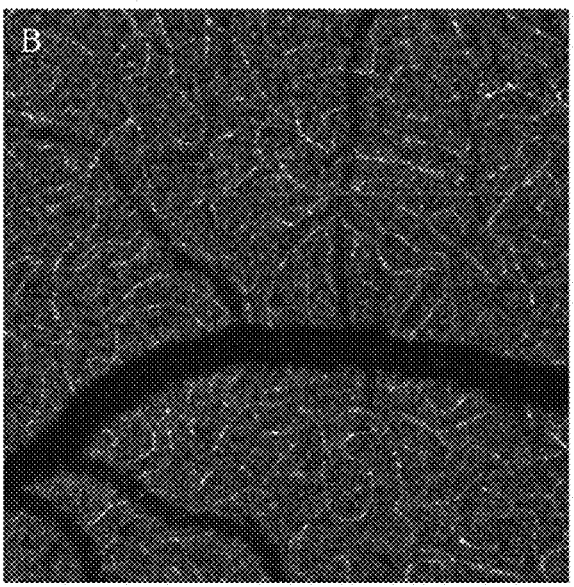
Figure 3D:
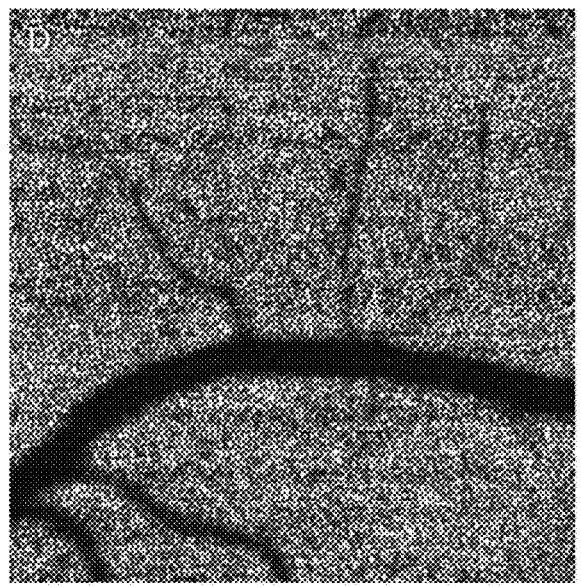

Disclosed are methods and systems for volumetric and/or depth-resolved figures of merit to guide optimization of aberrations in sensorless adaptive optics (AO)-optical coherence tomography (OCT) and/or AO-OCT angiography (AO-OCTA). The figure of merit may be generated in real-time, e.g., in parallel with the OCT scan and/or aberration optimization process.

Also disclosed herein is an exemplary system for acquiring and performing AO-OCT and/or AO-OCTA. The exemplary system comprises an OCT device configured to acquire OCT structural and angiography data in functional connection with a computing device having a logic subsystem and data holding capabilities. In embodiments the computing device is configured to receive data from the OCT device and perform one or more operations of the methods described herein.

In the following detailed description, reference is made to the accompanying drawings which form a part hereof, and in which are shown by way of illustration embodiments that can be practiced. It is to be understood that other embodiments can be utilized and structural or logical changes can be made without departing from the scope. Therefore, the following detailed description is not to be taken in a limiting sense, and the scope of embodiments is defined by the appended claims and their equivalents.

Various operations can be described as multiple discrete operations in turn, in a manner that can be helpful in understanding embodiments; however, the order of description should not be construed to imply that these operations are order dependent.

The description may use the terms "embodiment" or "embodiments," which may each refer to one or more of the same or different embodiments. Furthermore, the terms "comprising," "including," "having," and the like, as used with respect to embodiments, are synonymous.

In various embodiments, structure and/or flow information of a sample can be obtained using OCT (structure) and OCT angiography (flow) imaging-based on the detection of spectral interference. Such imaging can be two-dimensional (2-D) or three-dimensional (3-D), depending on the application. Structural imaging can be of an extended depth range relative to prior art methods, and flow imaging can be performed in real time. One or both of structural imaging and flow imaging as disclosed herein can be enlisted for producing 2-D or 3-D images.

Unless otherwise noted or explained, all technical and scientific terms used herein are used according to conventional usage and have the same meaning as commonly understood by one of ordinary skill in the art which the disclosure belongs. Although methods, systems, and apparatuses/materials similar or equivalent to those described herein can be used in the practice or testing of the present disclosure, suitable methods, systems, and apparatuses/materials are described below.

All publications, patent applications, patents, and other references mentioned herein are incorporated by reference in their entirety. In case of conflict, the present specification, including explanation of terms, will control. In addition, the methods, systems, apparatuses, materials, and examples are illustrative only and not intended to be limiting.

In order to facilitate review of the various embodiments of the disclosure, the following explanation of specific terms is provided:

A-scan: A reflectivity profile that contains information about spatial dimensions and location of structures within an item of interest. An A-scan is an axial scan directed along the optical axis of the OCT device and penetrates the sample being imaged. The A-scan encodes reflectivity information (for example, signal intensity) as a function of depth (z-direction).

B-scan: A cross-sectional tomograph that can be achieved by laterally combining a series of axial depth scans (i.e., A-scans) in the x-direction or y-direction. A B-scan encodes planar cross-sectional information from the sample and is typically presented as an image. Thus, a B-scan can be called a cross sectional image.

Dataset: As used herein, a dataset is an ordered-array representation of stored data values that encodes relative spatial location in row-column-depth (x-y-z axes) format. In the context of OCT, as used herein, a dataset can be conceptualized as a three dimensional array of voxels, each voxel having an associated value (for example, an intensity value, a complex value having both amplitude and phase information, a decorrelation value, or other signal representations). An A-scan corresponds to a set of collinear voxels along the depth (z-axis) direction of the dataset; a B-scan is made up of set of adjacent A-scans combined in the row or column (x- or y-axis) directions. Such a B-scan can also be referred to as an image, and its constituent voxels referred to as pixels. A collection of adjacent B-scans can be combined form a 3D volumetric set of voxel data referred to as a 3D image. In the system and methods described herein, the dataset obtained by an OCT scanning device is termed a "structural OCT" dataset whose values can, for example, be complex numbers carrying intensity and phase information. This structural OCT dataset can be used to calculate a corresponding dataset termed an "OCT angiography" dataset reflecting flow within the imaged sample. There is a correspondence between the voxels of the structural OCT dataset and the OCT angiography dataset. Thus, values from the datasets can be "overlaid" to present composite images of structure and flow (e.g., tissue microstructure and blood flow) or otherwise combined or compared.

En Face angiogram: OCT angiography data can be presented as a 2D projection of the three dimensional dataset onto a single planar image called an en face angiogram. Construction of such an en face angiogram requires the specification of the upper and lower depth extents that enclose the region of interest within the retina OCT scan to be projected onto the angiogram image. These upper and lower depth extents can be specified as the boundaries between different layers of the retina (e.g., the voxels between the inner limiting membrane and outer plexiform layer could be used to generate an en face angiogram of the inner retina). Once generated, the en face angiogram image may be used to quantify various features of the retinal vasculature as described herein. This quantification typically involves the setting of a threshold value to differentiate, for example, the pixels that represent flow within vasculature from static tissue within the angiogram. These en face angiograms can be interpreted in a manner similar to traditional angiography techniques such as fluorescein angiography (FA) or indocyanine green (ICG) angiography, and are thus well-suited for clinical use. It is also common to generate en face images from structural OCT data in a manner analogous to that used to generate en face angiograms. Angiograms from different layers may also be color-coded and overlaid to present composite angiograms with encoded depth information; structural en face images may also be included in such composite image generation.

Functional OCT, as used herein, broadly refers to the extension of OCT techniques to provide information beyond structural characterization. For example, whereas structural OCT imaging may be used to gather spatial information about a tissue's anatomical organization, functional OCT may be used to gather information about processes occurring within that tissue sample such as blood flow, tissue perfusion and oxygenation, birefringence, etc. Examples of functional OCT include, but are not limited to, OCTA and associated techniques for characterizing blood flow, Doppler OCT, polarization-sensitive OCT, OCT elastography, spectroscopic OCT, differential absorption OCT, and molecular imaging OCT.

AO-OCT and AO-OCTA is a technology to achieve high lateral resolution imaging of the retinal tissue and flow by compensating ocular aberrations. Wavefront sensors used to measure the optical aberrations of the eye increase the cost and footprint of the instrument, reduce the optical efficiency of the sample arm, and their accuracy is vulnerable to specular reflections from the lenses commonly used in an OCT sample arm. Conversely, sensorless AO-OCT may be used to estimate aberrations by producing volumetric OCT images in real time and generating merit functions based on image brightness to guide optimization algorithms.

Various embodiments may include a method to use one or more volumetric and/or depth-resolved figures of merit to guide optimization of aberrations in sensorless AO-OCT and/or AO-OCTA. The method may produce depth-resolved focusing for layer-specific optimization at arbitrary retinal depths. Additionally, or alternatively, the method may improve homogeneous optimization of the field of view (FOV) with respect to figures of merit based on a single B-scan.

In embodiments, the figure of merit may be generated in real-time, e.g., in parallel with the OCT scan and/or the optimization of aberrations. The figure of merit may be volumetric (e.g., to enable optimization over an entire FOV) and/or depth-resolved (e.g., allowing optimization focusing for specific layers or plexuses). This is significant because while the depth of focus in commercial OCT/OCTA encompasses the full retinal width, adaptive optics sacrifices the depth of focus to achieve better lateral resolution, yielding defocused images of the layers that are not optimized.

Accordingly, embodiments may enable the figures of merit to be generated at a high speed. This is possible due to high-speed scanning, real-time generation of OCT images with parallel computation, and/or real-time segmentation of the retinal depth of interest. This high-speed generation of the figures of merit may allow producing figures of merit of arbitrary layers, which is difficult without real-time segmentation. Previous systems optimize focusing for the bright ellipsoid-zone/retinal-pigment-epithelium complex and offset it manually to the retinal depth desired, which is both inaccurate and difficult to operate.

Optical wavefront aberrations can be expressed by Zernike polynomials or other mathematical representations such as Lukosz modes. The sensorless optimization of the wavefront aberrations may be achieved by iteratively find the optimal coefficient for these modes that describe the aberrations. For example, embodiments include an aberration optimization method based on hill-climbing with adaptive step size determined by the cumulative gradient sign, assisted by parabolic fitting of an objective function. The method may use the figure of merit to find the optimum point of the objective functions. The method may estimate the maximum value in a short time, thus allowing optimizing several aberrations (e.g., Zernike modes) within a tolerable scanning time. The method may guarantee sampling of the objective function within the dynamic range of the deformable element. Additionally, or alternatively, the method may alleviate hysteresis of the deformable element by sampling the objective function with adaptive, incremental steps. Furthermore, the method may enable easy exit of noise plateaus to guarantee reliable figures of merit. Accordingly, the method may ensure that extreme values in the dynamic range of the deformable element are not sampled (which may yield to low signal-to-noise ratio and thus unreliable figures of merit), misguide the optimization search towards noise plateaus, and/or introduce errors in the sampling of the effective region of the objective function due to high hysteresis.

While embodiments herein are described with reference to Zernike modes, the techniques may be used with other representations of ocular aberrations, such as Lukosz modes.

The hill-climbing method described herein is faster than traditional sensorless AO alternatives, providing a strong translational advantage. The alternative exhaustive search of the maximum value of the merit function across the entire dynamic range of deformable mirror peak-to-valley strokes for each Zernike mode (e.g., coordinate search) is slow and not feasible for clinical applications. The method described herein also shows a high success rate.

Moreover, the method may include an estimation (e.g., a digital estimation) of the maximum FOV for which aberrations can be optimized homogeneously, e.g., without requiring additional scans and therefore longer patient cooperation. This estimation of FOV may adapt the scanning size to different retinal curvatures to ensure the entire FOV including the corners of the images yield outstanding optical resolution. The FOV estimation may considerably reduce the number of volumetric scans that would otherwise be necessary to characterize each aberration for each possible FOV with coordinate-search sweeps.

Furthermore, embodiments may include Maximization of depth of focus by modifying the spherical aberration using real time, depth resolved pair-wise optimization of two retinal slabs. The composed depth-resolved figures of merit of different retinal layers generated and segmented in real time may help optimize the spherical aberration modes to enlarge the depth of focus of AO-OCT and/or AO-OCTA in order to achieve simultaneous high-resolution visualization of different layers or plexuses.

To the best knowledge of the inventors, the estimation in real time of the size of the retinal area for which aberrations can be optimized homogeneously has not achieved in vivo until now. Simulations of an isoplanatic FOV may be done prior to scanning using numerical model eyes, but these assumptions cannot be adapted with confidence to the specific retinal curvatures of each of the many eyes imaged in vivo every day in a clinical setting. This feature also helps to reduce the number of adjacent scans that need to be acquired in widefield AO-OCT/OCTA montaging.

While spherical aberration has been proposed to extend the depth of focus, previous implementations have relied on manual estimation and subjective evaluations. The optimization of composed depth-resolved figures of merit allows an automatic numerical estimation of the aberration amplitude that needs to be introduced to generate the largest depth of focus that preserves lateral resolution.

Various embodiments, example implementations, and example experimental results of AO-OCT and AO-OCTA are described further below.

Depth-Resolved Optimization of Real-Time Sensorless Adaptive-Optics Optical Coherence Tomography As discussed above, sensorless AO-OCT is a technology to image retinal tissue with high resolution by compensating ocular aberrations without wavefront sensors. Embodiments herein provide a fast and robust hill-climbing process to optimize multiple ocular aberrations (e.g., Zernike modes) in AO-OCT. The process is described in the example implementations below to compensate for five aberrations. However, the number of aberrations optimized by the process may be any suitable number, such as 2 to 10, 2 to 20 or more aberrations (e.g., depending on the desired/tolerable scanning time). The process may use a numerical aperture between that of conventional AO and commercial OCT systems. The merit function may be generated in real time (e.g., using a graphics processing unit (GPU)) while axially tracking the retinal layer of interest. Additionally, embodiments include a method to estimate the largest achievable field of view for which aberrations are corrected uniformly in sensorless AO-OCT.

Despite the outstanding resolution achieved with AO-OCT, its translation from bench to clinic has been challenged by a number of factors including large instrument footprint, high cost, narrow FOV and limited depth of focus. In addition, AO-OCT has historically required long imaging sessions and very cooperative subjects.

Various embodiments herein may improve the sensorless AO-OCT aberration estimation aiming to overcome some of the challenges of AO-OCT clinical translation. Embodiments may include an aberration correction method based on adaptive hill-climbing optimization of merit functions generated in real-time on GPU and calculated by projections of OCT reflectance (e.g., at a rate of 33 volumes per second or another suitable rate) while axially tracking the retinal depth of interest.

Wavefront sensors used to measure the optical aberrations of the eye increase the cost and footprint of the instrument, reduce the optical efficiency of the sample arm, and their accuracy is vulnerable to specular reflections from the lenses commonly used in an OCT sample arm. Conversely, sensorless AO-OCT can estimate aberrations by producing volumetric OCT images in real time and generating merit functions based on image brightness to guide optimization algorithms. This process is typically slower than sensor-based optimizations. Because the main disadvantage of sensorless AO-OCT is its relatively slow convergence, a fast and robust aberration estimation algorithm is paramount in sensorless schemes. Exhaustive search of the maximum value of the merit function across the entire dynamic range of deformable mirror peak-to-valley strokes for each Zernike mode (e.g., coordinate search) is slow and not feasible for clinical applications. The optimization process described herein may use a hill-climbing approach with adaptive step size based on the cumulative gradient sign, that searches for the optimal merit function of one or more (e.g., five) Zernike modes sequentially.

For example, FIG. 1 illustrates a process 100 for Hill-climbing algorithm optimization of one Zernike mode, in accordance with various embodiments. Every 30 ms, a merit function (MF) value is generated by the average projection of a depth-resolved slab of interest from real-time OCT volumes computed in a GPU. For example, at 102, the variables may be initialized, and a MF value generated. In one example, nine MF are sampled per Zernike mode. After the first iteration an adaptive step may be applied (e.g., at 104) to the deformable mirror stroke depending on the sign of the MF gradient. For example, at 106 of the process 100, it may be determined whether the MF gradient is greater than 0. If no, then the process 100 continues to block 108 to determine whether a trigger event is present (e.g., if it is the second consecutive negative gradient), as discussed further below. If the MF gradient is greater than 0, then at 110, it is determined whether the process 100 has reached the maximum step size. If not, the step size is set to twice the prior step size. If the step size has reached the maximum step size, the step size is maintained and the stroke is reset (at 112) to be stroke (current max MF) plus a value E.

Block 108 may be included to detect a special case based on a trigger event (e.g., in the event of two consecutive negative gradients) to exit noise plateaus. Other trigger events and/or number of consecutive negative gradients may be used in some embodiments. In some embodiments, if the trigger event is detected, the process 100 may proceed to block 112 to reset the stroke of the mirror.

In embodiments, a parabolic fit triggered by a simultaneous negative gradient and crossing of the current maximum MF estimates an optimal stroke that is never outside the mirror's dynamic range. For example, at 114 of the process 100, it may be determined if the MF value of the present iteration is greater than the current maximum MF (e.g., from prior iterations of the process 100). If no, the step size is set to a first value, which may be a negative fraction of the current step size (e.g., —step/3, as shown in FIG. 1). If yes, then a parabolic fit is triggered (at 116). Additionally, the step size may be set to a second value, which may be a positive fraction of the current step size (e.g., step/5, as shown in FIG. 1).

In various embodiments, the number of iterations, maximum step allowed, and/or value of E for the process 100 may be determined empirically from a model eye. The process 100 may be repeated for multiple Zernike modes, such as five Zernike modes.

Hill climbing may be assisted by parabolic fitting of the objective function and converged within a maximum of nine steps before proceeding to optimize the next mode. This scheme avoids hysteresis effects caused by large peak-to-valley stroke returns from the maximum permitted. Moreover, incremental hill climbing steps ensure the search is restricted to the dynamic range of the deformable mirror, and guarantee enough signal to noise ratio to segment the depth of interest accurately, thereby producing reliable merit functions of arbitrary depths to guide the optimization. In one example, a total of 5 modes were optimized in 1.35 seconds, considerably less than the time of average tear film breakup.

In one example implementation, the process was implemented in a spectral-domain sensorless AO-OCT prototype with a deformable mirror used as wavefront-correction element (DM69, ALPAO), for which a Zernike-to-command matrix was calibrated by factory. The illumination beam of most ophthalmic OCT devices is typically 1.0-1.3 mm diameter, for which ocular aberrations other than defocus have a negligible effect. Larger diameters allow higher lateral resolution using AO, but reduce the achievable FOV, typically limited between 0.5°-2° for a pupil size of 6 mm. In the example implementation, a 3.2 mm beam at the pupil was used as a tradeoff on lateral resolution to increase the FOV of AO-OCT for imaging of inner retinal elements (e.g. capillaries, nerve fibers) and the photoreceptor mosaic outside the central macula. The instrument's central wavelength was 840 nm with 91 nm bandwidth. The power incident on cornea was 0.77 mW. The lateral resolution was 6 µm and the estimated depth of focus was 58 µm.

The deformable mirror had 69 elements and could adjust up to 36 Zernike modes. Given the intermediate numerical aperture, only five modes were optimized—e.g. defocusing, oblique astigmatism, vertical astigmatism, horizontal coma, and vertical coma—in order to complete the optimization in a reasonable time. With an A-line acquisition speed of 250 kHz, 33 volumes/s could be acquired in the wavefront optimization process (high-speed mode) prior to acquisition, using a bidirectional scanning pattern and a scanning density of 150 A-lines per B-scan and 50 B-scans per volume. The deformable mirror allows defocus/astigmatism peak-to-valley strokes larger than 25 µm, with a resonant frequency of 1.2 kHz, and a maximum settling time of 450 µs. Volumes acquired in high-speed mode had higher sampling density in the fast-scanning direction than the low scanning direction to ensure accurate tracking of the layer of interest in real time on a B-scan basis. The mean value of the reflectance projection within the slab of interest was used as merit function. OCT volumes were processed in real time with GPU OCT software on a batch basis and the batch processing scheme allowed a relatively short overhead between acquisition and processing which is crucial for imaged-based sensorless AO.

Figure 4:
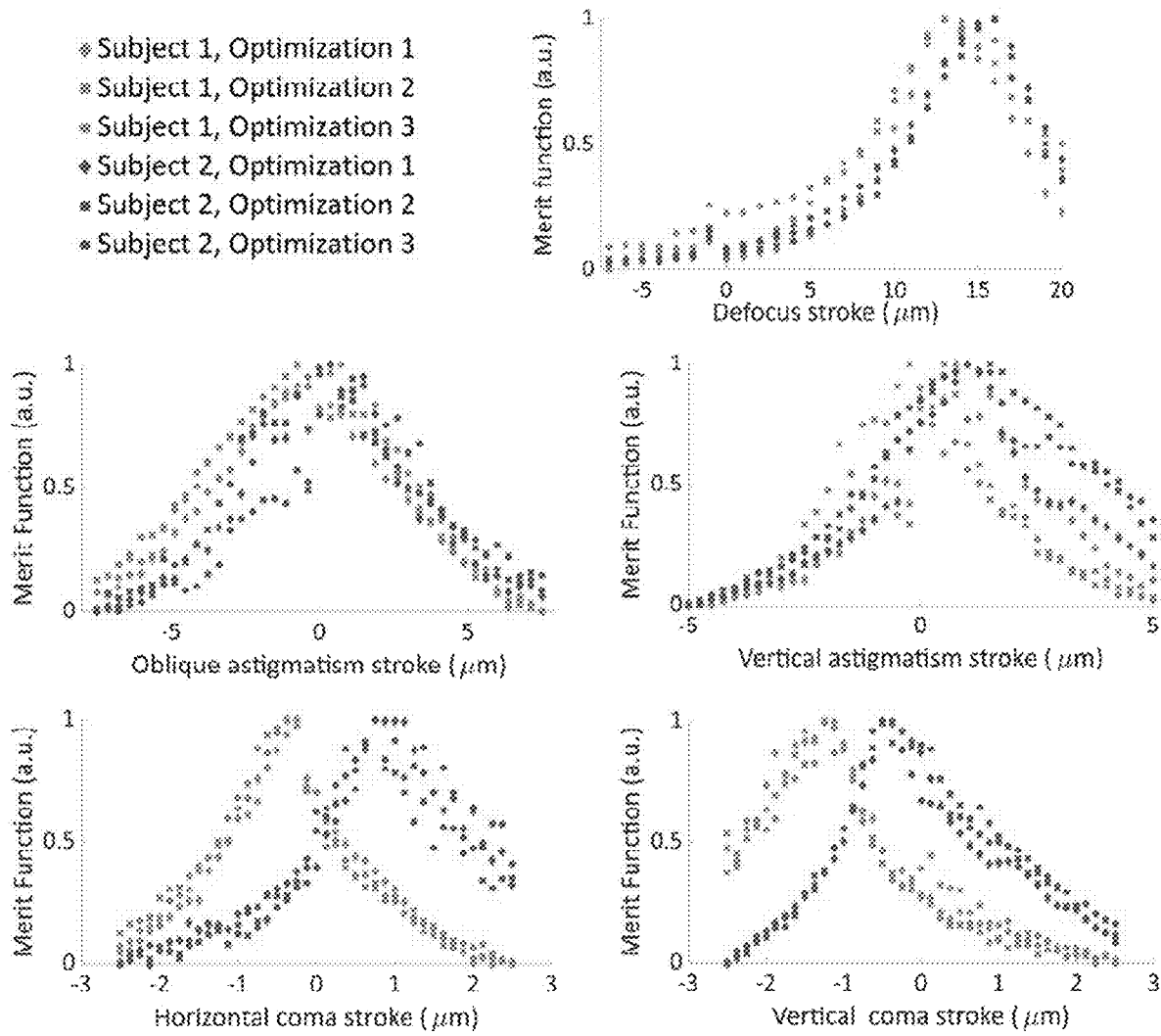
FIG. 4 illustrates evaluation of the stability of the merit function calculated in real time by the median of en face projection of the volumetric slab of interest in vivo in a healthy eye, in accordance with various embodiments. For the five Zernike modes described further herein, the Zernike mode amplitude was swept stepwise across the dynamic range of the deformable mirror. This was repeated three times separated by a blink for two eyes, each time describing a unimodal objective function and converging to the same peak-to-valley stroke within a standard deviation margin of 0.5 μm.

As shown in FIG. 2, the optimization of the adaptive hill climbing algorithm converged close to the peak of the objective function characterized by an exhaustive coordinate search within nine sampling points. The sequential optimization of five modes for the ellipsoid zone and the outer plexiform layer are shown in FIG. 3. Boundaries on the search of Zernike mode amplitudes were imposed according to measured system aberrations and literature reports of the aberration ranges found in human eyes. Subjects could blink between the aberration estimation routine and the AO-OCT acquisition. The objective function was unimodal for all modes optimized and highly reproducible between blinks (see FIG. 4).

Sensorless AO can approximate aberrations numerically but needs real time generation of reliable merit functions to guide the optimization routine. Due to the limited depth of focus of AO-OCT, a merit function guiding the wavefront phase optimization process may be computed using information restricted to the layer under scrutiny—photoreceptors, ganglion cells, nerve fibers, etc. —located at different retinal depths. In an example, axial tracking of the layer of interest was achieved by locating the brightest layer across the B-scan and applying user-selected axial offset. Higher sensitivity to eye motion, occasional errors in real-time segmentation of the retinal depth of interest and the finite settling time of the deformable mirror limit the robustness of relying on single B-scans for wavefront optimization. The "volumetric" merit function used here demonstrated excellent reproducibility (see FIG. 5A) and allowed visualization of individual nerve fibers and photoreceptors at 5 degree eccentricity nasal from the fovea center (see FIGS. 5B-5I). Because the depth of focus for the 3.2-mm beam is 58 µm, layer-specific focusing may be used for high-resolution visualization of inner/outer retinal elements. If the retinal depth is not accounted for in the merit function, the optimization may be biased to the photoreceptors.

In a population of seven eyes with refractive error between 0 and 3 diopters and astigmatism in a range of 0 to 0.5 diopters, the focusing correction step improved the merit function value by (mean±standard deviation) 30%±24% ($p<0.01$), the oblique astigmatism correction by 10±8% ($p<0.01$), the vertical astigmatism correction by 29%±22% ($p<0.01$), the horizontal coma correction by 7%±15% ($p<0.01$) and the vertical coma correction by 3%±6% ($p<0.01$). After optimization and acquisition, image quality could be evaluated by brightness, calculated as the averaged reflectance value; contrast, calculated as the standard deviation of the reflectance value; and sharpness, calculated as the mean gradient G as $$\sum \sum \frac{\sqrt{G_x^2 + G_y^2}}{m*n},$$

where m, n are the number of pixels over x and y axes. The brightness, contrast and sharpness of the NFL in NFL-specific optimization were improved by 49%±29%, 30%±39%, and 33%±31% respectively with respect to EZ-specific optimization, whereas for the EZ in EZ-specific optimization they were improved by 21%±44%, 38%±50%, and 51%±52% respectively with respect to NFL-specific optimization.

A significant hurdle to the successful clinical translation of AO-OCT is its limited FOV. Although it is possible to montage adjacent scans, the number of acquisitions needed can be reduced if each scan is acquired over the maximum FOV for which aberrations can be uniformly compensated. Such FOV can be defined as the area over which aberrations do not change significantly. Thus, in embodiments, the maximum area over which rectangular section sub-FOVs contained in the en face reflectance projection may describe the same aberration evolution as a reference central window. This approach considerably reduces the number of volumetric scans in high-speed mode that would otherwise be necessary to characterize each aberration for each possible FOV with coordinate-search sweeps.

As shown in FIGS. 6A-6G, a 3×3 mm² FOV was optimized with hill climbing and the merit function evolution over time was analyzed for sub-FOVs. The merit function (FIG. 6G) of the central 1×1 mm² FOV was cross-correlated with external rectangular sections (FIG. 6F, e.g. the area between blue and red, red and orange, etc.) to determine whether their trends can be considered the same (cross-correlation>0.95). By this method, the maximum FOV was determined for arbitrary retinal curvatures prior to acquisition.

Merit functions guiding sensorless AO-OCT should be robust to noise such as fixation drifts, potential tracking errors of the layer of interest and microsaccadic motion during the 1.35 seconds of optimization. In addition, and as seen in the en face projections generating the merit function (e.g., FIGS. 6A-F), large vessel sections entering and exiting the FOV due to drifts can cause significant reflectance variations, potentially affecting the reproducibility of the merit function, which is computed by averaging reflectance values. In embodiments, a factor that allows good stability includes calculating the merit function from volumetric projections rather than individual B-scans. By tracking the merit function over 27 consecutive measurements after completing optimization and without changing the deformable mirror stroke (FIG. 6G), a coefficient of variation of only 2.5% was measured.

A few previous optimization algorithms have been investigated to correct aberrations without wavefront sensors. Some alternatives based on gradient descent, an annealing algorithm, and data-based online nonlinear extremum-seeker (DONE) have been proposed, however they did not guarantee the convergence and were only suitable to optimize the brightest layers. In accordance with various embodiments herein, a merit function produced with (1) reliable axial tracking of the depth of interest and (2) robust to ocular motion during aberration correction, can reliably estimate an unknown objective function in vivo and can be easily optimized with an adaptive-step hill climbing approach in only 1.35 seconds. Any arbitrary retinal depth may be optimized automatically based on the corresponding depth-tracked merit function, which is faster and more reliable than manual tuning by an operator in either sensor-based or sensorless AO-OCT. The ability to reliably optimize the inner retinal layers and the resolution/field-of-view compromise in the instrument design will make this machine and method suitable for high-resolution imaging of inner retinal capillary flow with OCT angiography.

Techniques for AO-OCTA

OCTA can image the retinal blood flow but visualization of the capillary caliber is limited by the low lateral resolution. Adaptive optics (AO) can be used to compensate ocular aberrations when using high numerical aperture (NA), and thus improve image resolution. However, previously reported AO-OCTA instruments were large and complex, and have small sub-millimeter FOV that hinders the extraction of biomarkers with clinical relevance.

Various embodiments herein provide a sensorless AO-OCTA system with an intermediate numerical aperture to produce depth-resolved angiograms with high resolution and signal-to-noise ratio. In embodiments, the angiograms may have a 2×2 mm FOV, with a focal spot diameter of 6 µm, which is about 3 times finer than typical commercial OCT systems. These parameters may represent a better tradeoff between resolution and FOV compared to large-NA AO systems, since the spot size matches better that of capillaries. The system corrects defocus, astigmatism, and coma using a figure of merit based on mean reflectance projection of a slab defined with real-time segmentation of retinal layers. AO correction with the ability to optimize focusing in arbitrary retinal depths—particularly the plexuses in the inner retina—may be achieved in 1.35 seconds. The AO-OCTA images show greater flow signal, signal-to-noise ratio, and finer capillary caliber compared to commercial OCTA. Projection artifacts are also reduced in the intermediate and deep capillary plexuses. The instrument described here improves OCTA image quality without excessive sacrifice in FOV and device complexity, and thus may have potential for clinical translation.

Over the past decade, OCTA has been developed and gained in popularity for retinal imaging. Unlike fluorescence angiography, OCTA does not require intravenous dye injections and uses intrinsic motion contrast provided by the flowing blood cells. OCTA is acquired within a few seconds; making it ideal for translation into routine ophthalmic clinical practice. OCTA's three-dimensionality allows depth-resolved visualization of separate retinal plexuses and the choriocapillaris, although projection artifacts pose a problem that needs to be dealt with in post-processing. OCTA has been used to show capillary detail of the retinal vasculature or lack thereof, providing unprecedented details of neovascularization in diabetic retinopathy and age-related macular degeneration (AMD) as well as quantifiable differences in capillary perfusion or vascular topology of diseased and healthy eyes.

The rapid adoption of OCTA has been made possible by numerous hardware and software improvements. Novel algorithms that extract motion contrast from repeated B-scans have been successfully translated into commercial systems. Two- and three-dimensional registration methods have improved the signal-to-noise ratio (SNR) of prototypes and commercial systems by averaging. On the hardware side, the speed has doubled every two years allowing larger fields of view. Real time streaming and processing of images has become possible allowing better quality acquisitions, and tracking devices have been incorporated. Additionally, novel scanning protocols have been explored to reduce the prevalence of ocular motion artifacts, to increase the dynamic range, and to obtain velocimetric angiography.

One outstanding problem is the optical resolution of the instruments. The axial resolution in OCT depends on the central wavelength and bandwidth, whereas the lateral resolution depends on the NA of the imaging system, the aberrations introduced by ocular imperfections and the chromatic aberrations introduced by the source bandwidth. High lateral resolution is achieved by increasing the NA and using adaptive optics to compensate aberrations. Although AO-OCTA showing the true caliber of retinal capillaries has been demonstrated, the achievable FOV were significantly limited. Insufficient FOV sets limitations on the clinical applicability of OCTA. There are fundamental tradeoffs between resolution and FOV. Higher NA and resolution is tied with smaller isoplanatic patches that limit the FOV in which the beam can be sharply focused. Smaller spot diameter also requires higher scanning density, which limits the achievable scan area within a tolerable scan time, which is generally 3-4 seconds without blinking.

OCT systems described in the literature have so far clustered in the extreme ends of the tradeoff. Laboratory AO-OCT prototypes generally employed a high-NA, with the pupillary plane beam diameter of about 6 mm. These systems can produce outstanding resolution, but with limited FOV of less than 1 mm. On the other extreme, commercial OCT systems generally employ a low-NA, with the pupillary plane beam diameter of 1 to 1.2 mm. This allows a FOV of many mm but a focal spot size on the retinal plane of 15 to 20 µm, which is at least 2 times larger than capillary diameters. We believe the optimal trade-off for OCTA may lie in an intermediate NA that produces a focal spot diameter that is commensurate with capillary caliber of 4-7 µm.

Embodiments herein provide an intermediate-NA AO-OCTA instrument. The described instrument may image the parafoveal circulation within 3 seconds. The intermediate NA requires the correction of relatively fewer modes of higher-order aberrations, which is suitable for a sensorless design. Sensorless AO has several translational advantages over wavefront sensor-based instruments. The optical hardware complexity and cost is lower since the sensor, coupler, and many relay mirrors could be obviated. The footprint is further reduced because the optical design is based primarily on lenses rather than mirrors. However, sensorless AO comes with its own unique set of requirements. It relies on rapid estimation of the objective function to optimize focusing for specific tissue layers.

Embodiments include a fast and effective hill-climbing optimization process with adaptive step size to compensate aberrations prior to OCTA acquisition with the prototype instrument. For example, the hill-climbing optimization method described above and depicted in FIG. 1 may be used in some embodiments. Five low order Zernike modes may be compensated within 1.35 seconds. This sensorless AO system may incorporate real-time segmentation of the retinal layers, which allowed us to focus on the inner layers where retinal plexuses reside. This is yet another advantage over previous wavefront optimization mechanisms that tended to optimize focusing to the outer retinal layers where reflectance is strongest. As described further below, the sensorless AO-OCTA instrument benefits in producing OCTA images with improved contrast, SNR, and visualization of capillary caliber, as well as reduced prevalence of projection artifacts, all of that with a moderate sacrifice in FOV.

MATERIALS AND METHODS

Data Acquisition

Figure 7A:
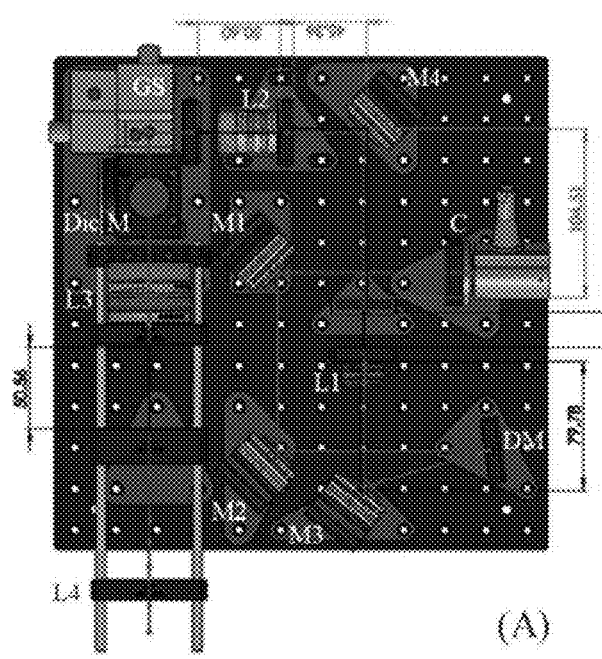
FIGS. 7A and 7B illustrate a setup of the sample arm of AO-OCTA system, in accordance with various embodiments.
Figure 7B:
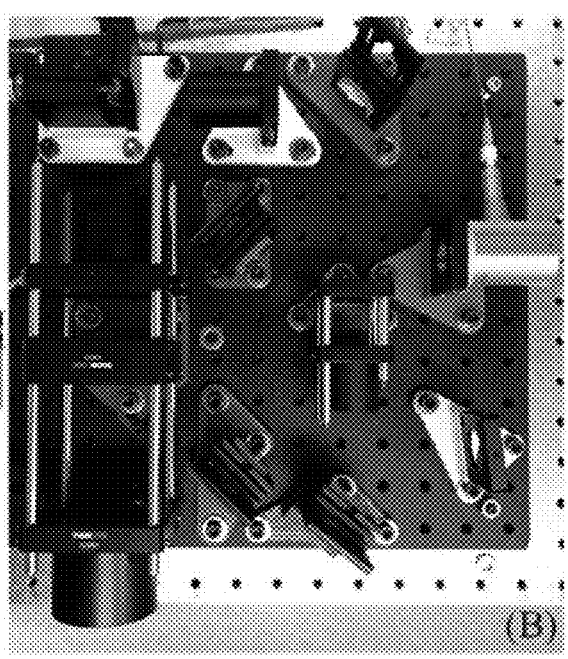

Subjects were scanned over 0.75×0.75 mm, 1.5×1.5 mm, 2×2 mm, and 3.3×3.3 mm FOVs in a single shot with a 250-kHz AO-OCTA prototype built at the Center for Ophthalmic Optics and Lasers (COOL Lab) of the Casey Eye Institute. FIG. 7A is a CAD drawing of the AO-OCTA instrument, and FIG. 7B is a photo of the instrument on a breadboard. The components labeled in FIG. 7A include: C—Reflective collimator (Thorlabs, Inc.) M1-M4—Mirrors. L1-L4—Lenses with focal length of 150 mm, 60 mm, 100 mm and 75 mm respectively. GS—Galvo scanner (Cambridge Technologies). DM—Deformable mirror (DM69, ALPAO, Inc.). Dic M—Dichroic mirror redirecting visible light to an upper level with the fixation target. A spectrometer (Cobra-S 800, Wasatch photonics) with a 2048-pixel camera (Octoplus, Teledyne e2v) was used to read the OCT interferograms. Optical fiber patches were added to the sample and reference arms to compensate delay and dispersion. A dummy mirror was placed at the position of the deformable mirror in the picture for alignment purposes. Spacers were 3D printed. The sample arm efficiency was 75%. It will be apparent that modifications to the system shown in FIGS. 7A and 7B may be made in accordance with various embodiments. For example, one or more components may be substituted with one or more other suitable components, one or more components may be omitted, and/or one or more components may be added.

All FOVs were acquired with scan density of 600 A-lines×1200 B-scans, which includes two repetitions at each B-scan position. Scans sized 2×2 mm centered on the fovea were also acquired with a 70-kHz commercial, spectral-domain OCT system (Avanti, Optovue, Inc., Fremont, CA), consisting of 304 A-lines×608 B-scans. Instead of placing the pupil-conjugated deformable mirror on axis and using the classic combination of a pair of wave plate and polarization beam splitter, the deformable mirror was placed at an incidence angle of 8 degrees (See FIGS. 7A and 7B) to reduce the optical losses of the sample arm. Besides the telescope placed to steer the beam through the pupil, another telescope was used to reduce the beam diameter from the aperture of the deformable mirror (10.5 mm) to the aperture of the galvo scanners (5 mm). The entire sample arm fit in a 12"×12" breadboard (see FIG. 7B).

Figure 8A:
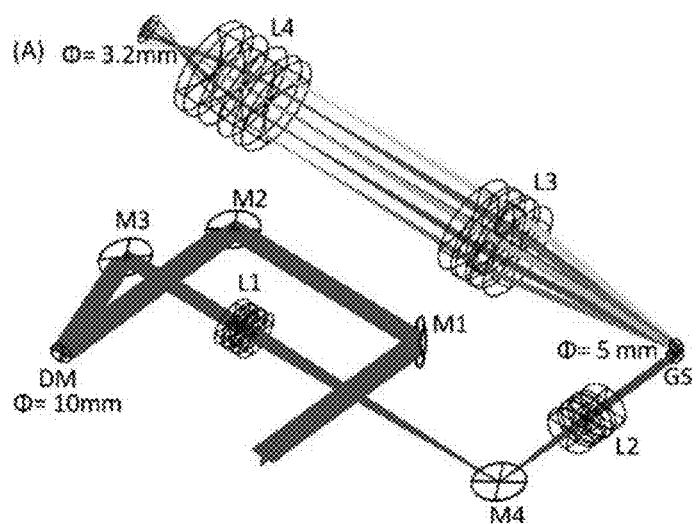
FIGS. 8A and 8B illustrate a simulation of the system's optical performance in OpticStudio (Zemax).
Figure 8B:
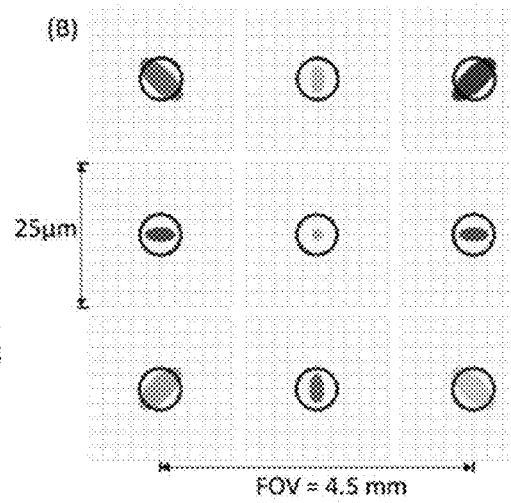

Both systems had light sources centered at 840-nm wavelength. The commercial system had a 50-nm bandwidth, yielding an axial resolution of 5 μm in tissue whereas the prototype's source had an effective 91-nm bandwidth, for an axial resolution of approximately 3 μm. The axial digital sampling was 3 μm for the commercial system and 2 μm for the prototype by using a Cobra-S 800 spectrometer (Wasatch photonics, Inc.) with a 2048-pixel camera (Octoplus, Teledyne e2v). In terms of lateral resolution, the prototype could correct five low-order aberrations by controlling a deformable mirror (DM 69, ALPAO Inc., France) containing 69 actuators that allowed a theoretical optical resolution of 6 μm (see FIGS. 8A-8B), whereas the commercial system's resolution was 15 μm. The system was designed with an intermediate NA of ~0.1 (beam diameter=3.2 mm on pupil) to reduce the visualized caliber of capillaries with respect to commercial OCTA and increase the FOV with respect to high-NA AO-OCT instruments; allowing single run, non-mydriatic scanning of a clinically useful FOV. The transverse sampling densities for the 2×2 mm scanning protocol were 6.5 μm/pixel for the commercial system and 3.3 μm/pixel for the AO-OCTA prototype. The tracking system available in the commercial system was activated to reduce the prevalence of motion artifacts.

Data Processing

Figures 9A, 9B, 9C:
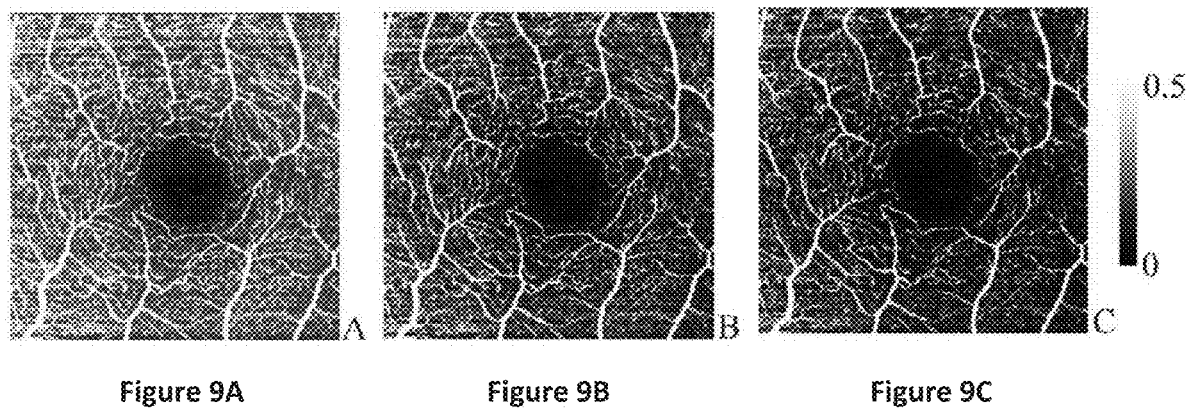
FIGS. 9A-9C illustrate that increasing the number of spectral splits with respect to previous split-spectrum amplitude decorrelation angiography (SSADA) implementations allowed increasing the flow signal-to-noise ratio (SNR) while maintaining the sharpness of capillaries in en face angiogram visualizations, in accordance with various embodiments. The superficial vascular complex is demonstrated. Flow SNR increases from 5.6 for the 11 spectral splits (FIG. 9A, bandwidth of 27 nm, separated by 6.6 nm) to 9.5 for 18 spectral splits (FIG. 9B, bandwidth of 20 nm, separated by 4.3 nm) and 11.2 for 23 spectral splits (FIG. 9C, bandwidth of 18 nm, separated by 3.5 nm). In the experimental results, a greater number of spectral splits did not yield further SNR improvement on en face OCTA projections. However, a different and/or greater number of spectral splits may be used in some embodiments.

Flow signal in both the prototype and the commercial system was generated by the split-spectrum amplitude-decorrelation (SSADA) algorithm (see Y. Jia, S. T. Bailey, T. S. Hwang, S. M. McClintic, S. S. Gao, M. E. Pennesi, C. J. Flaxel, A. K. Lauer, D. J. Wilson, J. Hornegger, J. G. Fujimoto, and D. Huang, "Quantitative optical coherence tomography angiography of vascular abnormalities in the living human eye," Proceedings of the National Academy of Sciences 112, E2395 (2015); and Y. Jia, O. Tan, J. Tokayer, B. Potsaid, Y. Wang, J. J. Liu, M. F. Kraus, H. Subhash, J. G. Fujimoto, J. Hornegger, and D. Huang, "Split-spectrum amplitude-decorrelation angiography with optical coherence tomography," Opt Express 20, 4710-4725 (2012), incorporated by reference herein), computed from the two overlapping B-scans acquired at each position. In SSADA, the speckle variances of OCT B-scans generated for different spectral bands of interferometric signal yielding the OCT B-scan images are averaged, improving the signal-to-noise ratio of flow detection over full-bandwidth speckle decorrelation measurement. Previous work using the commercial Avanti system has shown the number of spectral Gaussian splits for optimal SSADA implementation was 11. Because the AO-OCT prototype presented here has a wider spectrum, it allowed a larger number of splits. In this example implementation, twenty-three splits yielded the highest SNR (see FIGS. 9A-9C), each having a bandwidth of 18 nm with their centers separated by 3.5 nm from the neighboring Gaussian windows. It will be apparent that a different number of splits may be used in accordance with various embodiments.

Because AO-OCTA has a reduced depth of focus with respect to commercial OCTA, the focusing of acquisitions was optimized for the inner retinal layers (e.g., between the inner limiting membrane and the outer plexiform layer) where the retinal plexuses reside. Retinal layers were segmented using a U-Net type fully-convolutional neural network for en face projection presentation of the layers and plexuses of interest. Annotations for generating training datasets were obtained with a graph-cut algorithm and manual corrections. To make U-Net inferencing available in real-time, TensorRT was used to prune and fuse some of the layers in the implementation of U-Net, and reduced float32 precision to int8, while preserving the network performance. Tensor Cores in GPU were also used to increase substantially the speed of convolutional operations. Network training and inference was performed on B-scans after averaging 10 consecutive frames and performing rigid registrations to compensate moderate displacements between them caused by involuntary ocular motion.

Figure 10:
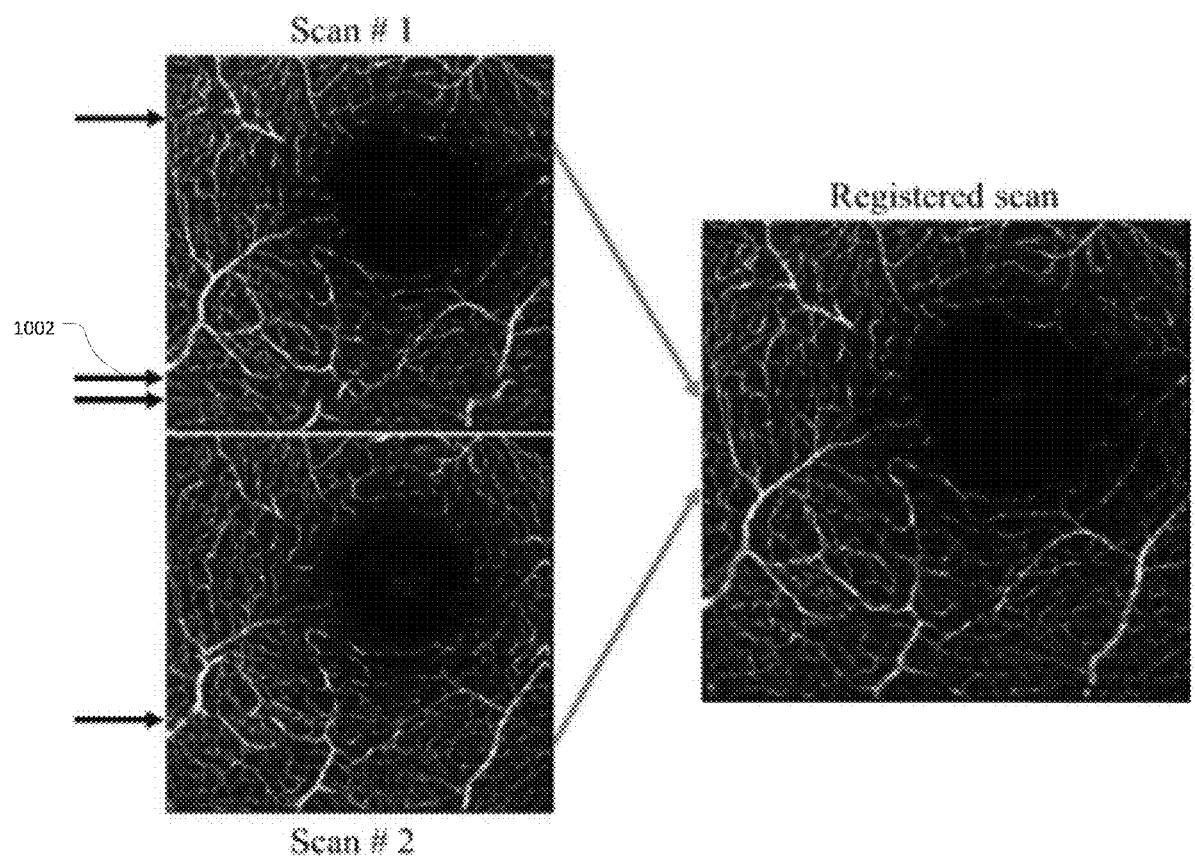
FIG. 10 illustrates removal of motion artifacts by parallel-strip registration of two redundant scans of the same FOV acquired with the AO-OCTA prototype system. Black arrows 1002 indicate the position of motion artifacts in the original scans.

En face images of the superficial vascular complex (SVC), intermediate capillary plexus (ICP) and deep capillary plexus (DCP) were generated by maximum projection of OCTA decorrelation values. In order to remove microsaccadic artifacts, two redundant OCTA scans of the same FOV were acquired and registered. For the AngioVue system, a proprietary registration algorithm merged two consecutive raster scans acquired in orthogonal scanning priorities. For the AO-OCTA prototype, these artifacts were removed by parallel strip registration (see FIG. 10; P. Zang, G. Liu, M. Zhang, C. Dongye, J. Wang, A. D. Pechauer, T. S. Hwang, D. J. Wilson, D. Huang, D. Li, and Y. Jia, "Automated motion correction using parallel-strip registration for wide-field en face OCT angiogram," Biomed Opt Express 7, 2823-2836 (2016); and M. Heisler, S. Lee, Z. Mammo, Y. Jian, M. J. Ju, A. Merkur, E. Navajas, C. Balaratnasingam, M. F. Beg, and M. Sarunic, "Strip-based registration of serially acquired optical coherence tomography angiography," Journal of Biomedical Optics 22, 036007 (2017); incorporated by reference herein).

Real time rendering of OCT and OCTA volumes on GPU was incorporated into the acquisition software OCTViewer, allowing video-rate streaming of OCT and OCTA cross-sectional and en face visualizations of AO prototype acquisitions. The desktop computer controlling the acquisition components contained an Intel Core i9 9900k CPU and a NVIDIA Titan RTX GPU, running on Windows 10 with CUDA release v10.2. Rather than saving the data captured after the operator clicks on acquisition, the AO-OCTA prototype operates in continuous acquisition mode and allowed the operator to wait for a high-quality scan and save the data currently present in the buffer. Continuously rendering the OCT and OCTA en face projections of the layer of interest as well as real-time streaming of B-scans helped the operator reduce the prevalence of blinks, motion and vignetting artifacts by improving the judgement of scan quality prior to acquisition.

Sensorless Optimization of Human Eye Aberrations by AO-OCTA Prototype

Figure 11:
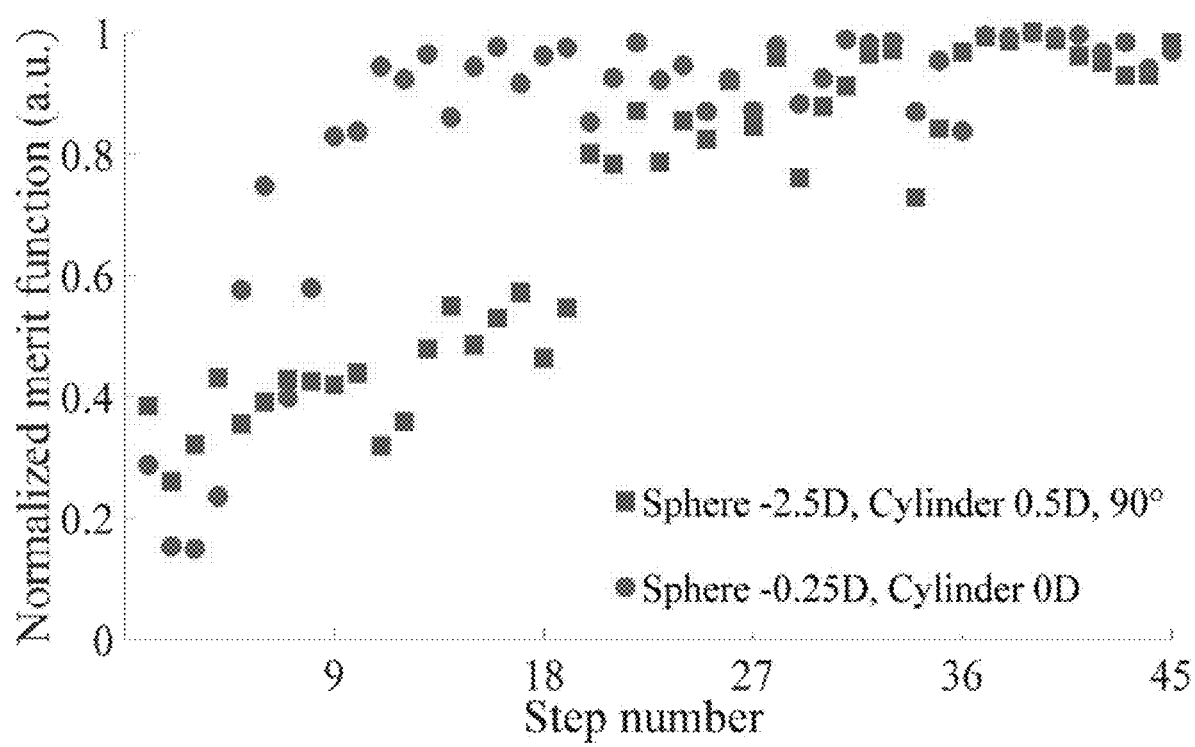
FIG. 11 illustrates a comparison of the figure of merit evolution normalized to its maximum value, during the optimization of ocular aberrations prior to OCTA acquisition for an astigmatic and a non-astigmatic subject. Each point represents the mean value of the reflectance OCT projection of the slab/layer of interest from a volume acquired in high-speed mode at a rate of 33 volumes per second. The non-astigmatic subject reached its optimal correction after the first mode (defocus, first nine steps), whereas the astigmatic subject reached its optimal correction after oblique and vertical astigmatism had been optimized (first 27 steps). The entire process (45 figures of merit computed, 9 per mode) was completed within 1.35 seconds.

The figure of merit used to guide the optimization of ocular aberrations was the average value of the mean reflectance projection within the slab of interest. It was calculated from undersampled OCT data acquired at a rate of 33 volumes/s. Nine figures of merit were acquired per Zernike mode, which estimated the critical point of objective functions for defocus, vertical and oblique astigmatism, and vertical and horizontal coma in a sequential fashion. Sensorless sampling of the unknown objective function was determined by a hill climbing optimization with adaptive step size, which uses the cumulative sign of the gradient to determine the step and is assisted by a quadratic fitting of three figure of merit values estimated to reside at the vicinity of the objective function critical point. Optimization took only 1.35 seconds (see FIG. 11), and the hill-climbing method minimized the detrimental effects of hysteresis and avoided searching near the end of the deformable mirror's dynamic range, where figures of merit cannot be produced reliably due to low signal quality. After optimization, subjects were allowed to blink before the subsequent OCTA acquisition took place. As discussed above, this sensorless optimization routine is highly reproducible between blinks and robust to involuntary ocular motion.

Quantitative Comparison with Commercial OCTA.

Images acquired by the commercial and AO prototype instruments were compared by flow SNR, prevalence of projection artifacts, capillary caliber, and vessel density. The flow SNR was found from the signal of the foreground (vascular pixels) and the signal of the 0.3-mm radius foveal avascular zone (FAZ), $$SNR = \frac{\overline{D} - \overline{D_{FAZ}}}{\sqrt{\sigma^2_{D_{FAZ}}}} \quad (1)$$

where $\overline{D}$ represents the mean decorrelation value and $\sigma_{D_{FAZ}}$ represents the standard deviation of the background decorrelation. The vessel density values were calculated from the binary vascular masks generated using a thresholding scheme based on the regression analysis of the relationship between decorrelation and reflectance of the background voxels (see A. Camino, M. Zhang, L. Liu, J. Wang, Y. Jia, and D. Huang, "Enhanced Quantification of Retinal Perfusion by Improved Discrimination of Blood Flow From Bulk Motion Signal in OCTA," Translational Vision Science & Technology 7, 20-20 (2018), incorporated by reference herein). It was calculated as the percentage of vascular pixels, excluding the central 0.6-mm diameter circular area co-centered with the FAZ.

The prevalence of projection artifacts was also compared between the two instruments. It has been demonstrated previously that AO-OCTA reduces the effect of this common artifact, which confounds the visualization and quantification of capillary perfusion in the ICP and DCP. This benefit of AO was attributed to the tighter depth of focus of the optical beam projected on the retina. In the present embodiment using a looser depth of focus than the prior technique, the prevalence of this artifact was investigated by computing the cross-correlation coefficient of the ICP and DCP with the SVC in both AO and commercial OCTA instruments. The vessel density was then compared with respect to the AO-OCTA images.

The capillary caliber yielded by both instruments was calculated by finding the ratio between the number of vascular pixels in the vascular binary masks and the number of pixels in a skeletonized binary mask.

A paired t-test was used to evaluate the statistical significance of all AO prototype and commercial OCTA comparisons.

Results

The retinal blood flow of eleven healthy eyes from eleven subjects (35±2 years old) with −1 to 3 diopters of defocus and −1 to 0.5 diopters of astigmatism was imaged with OCTA on both instruments over a 2×2 mm FOV centered at the fovea and focusing on the inner retina. These eyes were also imaged at different eccentricities (up to 5-degrees superior and nasal to the fovea) and fields of view (3×3 mm, 1.5×1.5 mm and 0.75×0.75 mm) with the AO-OCTA prototype only.

Because the depth-of-focus of the AO-OCTA prototype (58 µm) is shorter than the retinal width, layer-specific focusing was essential to maintaining good quality OCTA (see FIGS. 12A-12D). If the figure of merit used for optimization of defocus was dominated by outer-retinal reflectance values (see FIG. 12B), OCTA of the inner retinal flow would yield low quality en face angiograms (see FIG. 12D).

Figure 13:
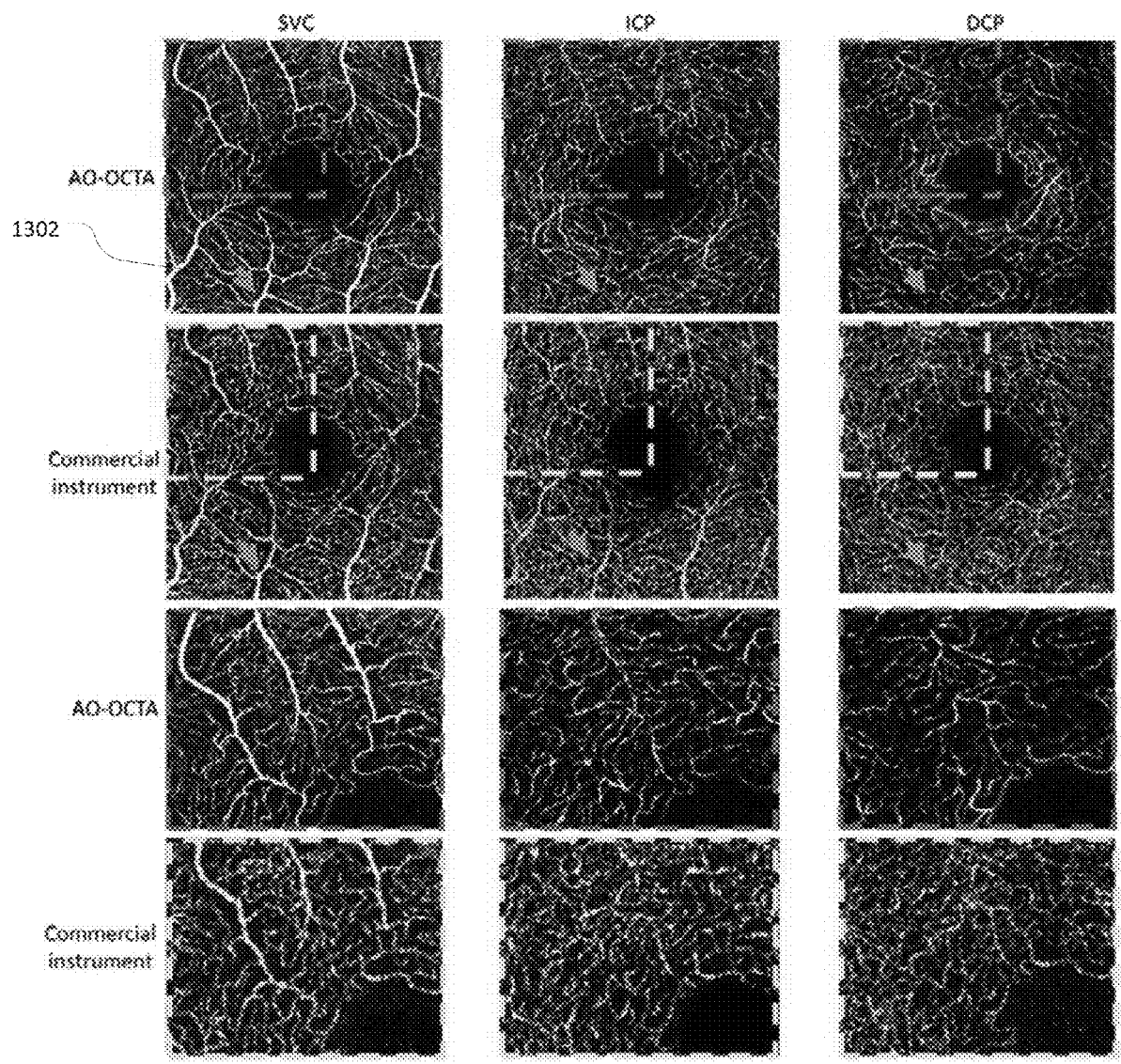
FIG. 13 illustrates that superficial vascular complex (SVC), intermediate capillary plexus (ICP) and deep capillary plexus (DCP) show better contrast in the images acquired by the AO-OCTA prototype compared to the images acquired by the commercial instrument. Upper-left corners were enlarged to better visualize the difference in contrast. Projection artifacts were visibly reduced (e.g. the locations marked by blue arrows 1302) by AO-OCTA without using any projection removal post-processing algorithm. FOV is 2×2 mm for both instruments.

Prevalence of projection artifacts measured as cross-correlation with SVC was reduced significantly by the AO-OCTA prototype with respect to the commercial instrument (blue arrows in FIG. 13) in both the ICP (AO-OCT 0.45±0.07 vs Commercial 0.69±0.02, p<0.01) and the DCP (AO-OCT 0.07±0.04 vs Commercial 0.35±0.07, p<0.01). The AO-OCTA instrument yielded higher contrast than commercial OCTA on this plexuses (p<0.01), visualized in higher detail in the areas surrounded by dashed lines in FIG. 13.

Figure 14:
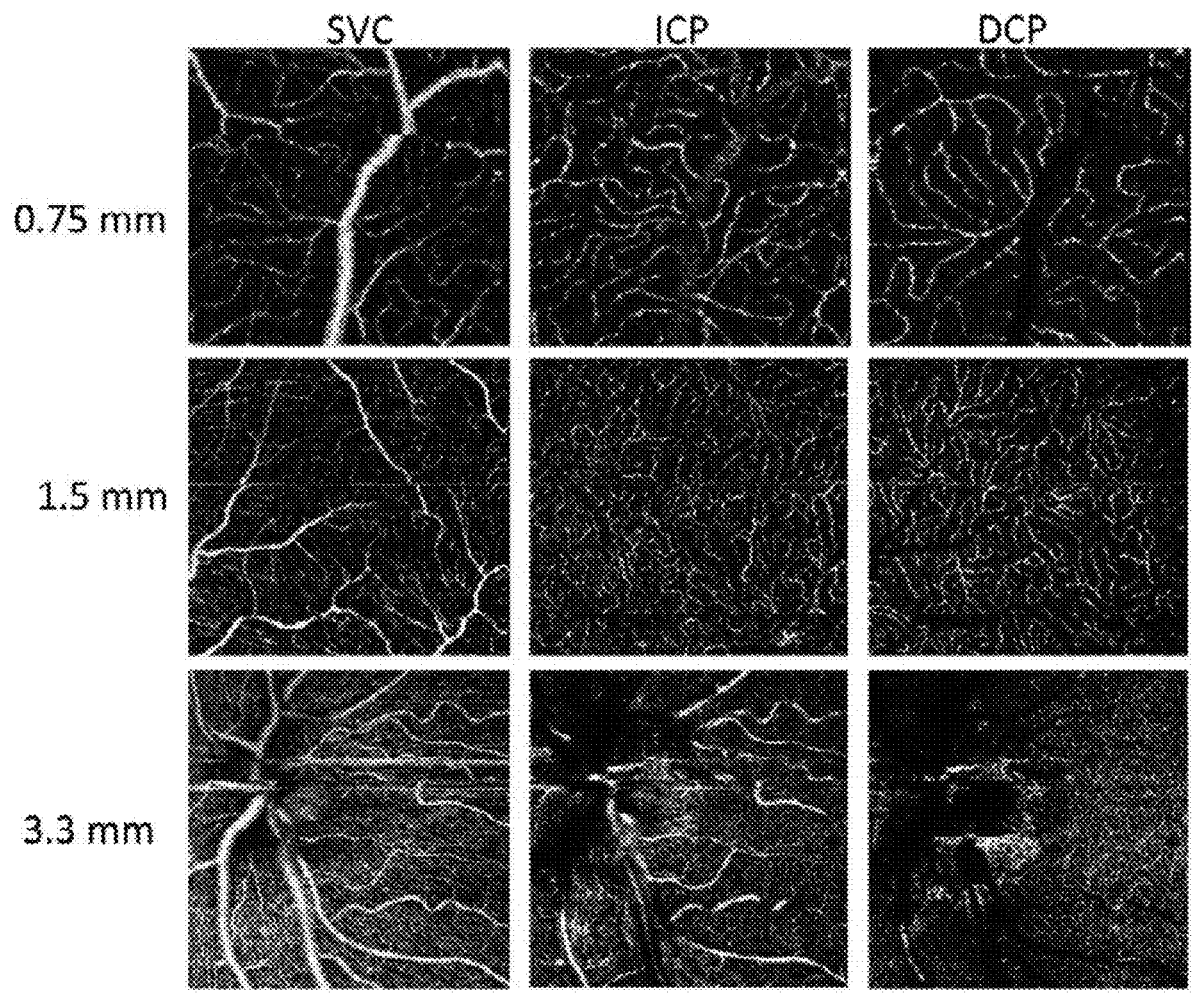
FIG. 14 illustrates OCTA of FOV of 0.75×0.75 mm at 5 degrees superior to the fovea, 1.5×1.5 mm at 5 degrees nasal to the fovea and 3.3×3.3 mm of the peripapillary area, acquired from an eye with −0.5 diopters of defocus and 0.25 diopters of astigmatism. High capillary contrast is observed for the superficial vascular complex (SVC), intermediate capillary plexus (ICP) and deep capillary plexus (DCP). The low prevalence of OCTA projection artifacts is visualized on ICP and DCP images.

The high capillary contrast and low correlation of the ICP and DCP with the SVC capillary networks was observed for all eccentricities and fields of view explored (see FIG. 14), including the most clinical useful landmarks, e.g., the parafoveal and peripapillary regions.

The vessel density measured by the AO-OCTA prototype was reduced for all plexuses (p<0.01, Table 1). Because the flow SNR was also considerably higher for AO-OCTA (Table 1), the reduction in vessel density could not be due to reduced OCTA signal. The combination of a thinner apparent capillary caliber and reduced prevalence of projection artifacts using adaptive optics worked together to reduce the measured vessel density. Indeed, the capillary diameters obtained by AO-OCTA (Table 2) lied between 7 µm and 9 µm—which are values closer to the real caliber, whereas the capillary diameter measured on OCTA produced by the commercial instrument was between 12-14 µm.

TABLE 1

Comparison of signal-to-noise ratio and vessel density between AO-OCTA and commercial OCTA.

| | Flow SNR* | Vessel density (%)* | | |
|---|---|---|---|---|
| | Inner Retina | SVC | ICP | DCP |
| AO-OCTA | 8.6 ± 3.3 | 23.3 ± 1.9 | 25.8 ± 1.7 | 25.0 ± 3.0 |
| Commercial OCTA | 1.0 ± 1.0 | 44.0 ± 7.4 | 36.0 ± 4.5 | 30.3 ± 2.9 |

*Scans of 11 healthy eyes over a 2 × 2 mm FOV centered at fovea

TABLE 2

Comparison of capillary caliber observed in the retinal plexuses with AO-OCTA and commercial OCTA.

| | Capillary caliber (µm)* | | |
|---|---|---|---|
| | SVC | ICP | DCP |
| AO-OCTA | 7.8 ± 0.6 | 8.4 ± 0.5 | 8.6 ± 0.5 |
| Commercial OCTA | 14.3 ± 0.7 | 12.9 ± 0.5 | 12.3 ± 0.3 |

*Scans of 11 healthy eyes over a 2 × 2 mm FOV centered at fovea

Figure 15:
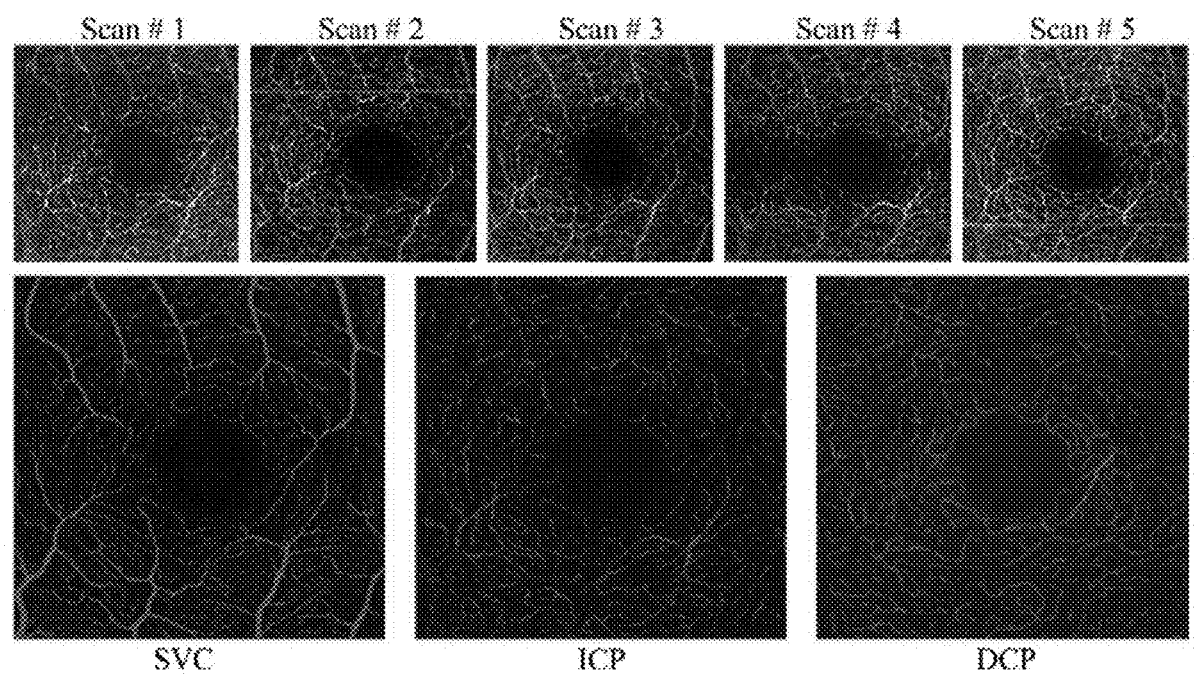
FIG. 15 illustrates parallel-strip registration of retinal angiograms of the SVC, ICP, and DCP acquired with the AO-OCTA prototype resulting in high contrast and removal of projection and vignetting artifacts observed with random prevalence in single scans. The top row shows inner retinal flow is represented in single scans in an RGB color scheme (red—SVC flow, green—ICP, blue—DCP).

Parallel-strip registration could also be applied for more than two scans (see FIG. 15). The real-time rendering feature of the acquisition software allowed the operator to wait for the right acquisition instant where the minimal amount of blinks and microsaccadic artifacts were present and acquire the data being rendered in real time. This reduced the probability of overlapping microsaccades, which challenges the success of parallel-strip registration.

Discussion

As discussed, embodiments herein provide a high-speed, spectral-domain sensorless AO-OCTA instrument to image retinal capillaries of all retinal plexuses simultaneously with high resolution. Improved visualization of the intermediate and deep plexuses with respect to commercial OCTA was demonstrated. With the addition of post-processing motion correction by parallel-strip registration, AO-OCTA provided depth-resolved and motion-artifact-free angiograms of the retinal blood flow with outstanding capillary resolution. Although the experimental results are provided for healthy eyes, the optimization of aberrations should also be successful in future imaging of diseases of interest such as diabetic retinopathy and AMD.

AO-OCTA improves the caliber of capillaries by refining the optical resolution of the scanning beam. Therefore, when the beam samples vascular pixels, the OCTA decorrelation is less likely diluted by the influence of adjacent static signal encompassed in the point spread function. Consequently, a larger SNR is observed for AO-OCTA images although (1) the inter B-scan time was half that of the commercial instrument and (2) higher resolution can also increase the background signal in the event of bulk motion during scanning or beam repositioning errors.

High-NA instruments designed for visualization of cone and rod photoreceptors can exhibit outstanding capillary resolution but reduce considerably the effective FOV and available depth of focus. The intermediate-NA system described herein may scan the retina with a beam spot of 6 µm, a diameter within the range of capillary thickness that allows larger FOV and depth of focus. The area covered by the FOVs demonstrated here is sufficient to extract foveal biomarkers and parafoveal perfusion density from OCTA, biomarkers with great potential in clinical evaluation. The 58 µm depth of focus was sufficient to image the three plexuses but it was still less than the whole retinal thickness. Thus, separate focusing would be needed to obtain high quality OCTA of outer retinal (e.g. choroidal neovascularization, CNV) and choriodal flow (e.g. choriocapillaris). This is a disadvantage in comparison to low-NA commercial OCTA systems, which could image both retinal and choroidal circulations simultaneously.

The capability to optimize defocus for any arbitrary layer has been a challenge for both censored and sensorless AO instruments. With the advent of high-speed OCTA systems and the use of GPU computation, it is now possible to optimize the inner retinal flow by minimizing aberrations using a three-dimensional figure of merit extracted from volumes acquired at a rate of several Hz and with real-time tracking of the retinal depth desired. Here, the sensorless optimization routine prior to OCTA acquisition took only 1.35 seconds to correct inner-retinal specific defocus together with oblique and vertical astigmatism, as well as horizontal and vertical coma. In contrast, commercial instruments not using adaptive optics only correct for defocus and need to reduce the NA in order to assume the remaining aberrations negligible.

Despite OCTA's advantages over fluorescein angiography, a historical limitation of OCTA has been the smaller FOV. Because of the constraint imposed by the shorter depth of focus, adaptive optics instruments restrain OCTA's FOV even further. The device described herein, based on intermediate-NA imaging beams, alleviates this problem and present a potential to either achieve a clinically useful FOV in a single scan or to reduce the number of acquisitions needed for larger FOVs by montaging partially overlapping scans. As discussed above, the inventors have estimated that for an intermediate NA instrument, aberrations can be compensated for homogeneously over a FOV up to 2.5 mm. Although that FOV for a single scan is about 4 times larger than typical AO, it is still smaller than the FOV currently achievable with commercial OCTA. Some clinical applications such as imaging the CNV in AMD might still require stitching with scans acquired at adjacent positions.

A limitation of the instrument presented here is the scanning speed. Although 250 kHz is for a spectral domain system higher than any speed commercially available, the smaller beam spot using AO demands a proportionally more sampling points, effectively increasing the volume acquisition time and consequently the prevalence of blinks and microsaccadic artifacts. With the scanning density used in the example implementation herein (600×600×2), an isotropic scanning pattern was completed with sufficient sampling and within approximately 3 seconds, which is a reasonable fixation time when tracking hardware is not used.

One benefit of AO-OCTA is the reduction of projection artifacts. This artifact manifests as a projection of the superficial vascular network flow signal on top of the underlying capillary plexuses, outer retina and choriocapillaris; hindering the visualization of in situ flow. Projections are reduced in AO-OCTA because with the tighter focusing achieved by the higher NA, the incident beam is less likely to be significantly perturbed by the moving blood cells in the superficial vessels during forward propagation. Projection-resolved OCTA (PR-OCTA) algorithms have been successfully implemented previously on commercial OCTA. These algorithms might occasionally remove true flow pixels affecting the vessel continuity, or be unable to remove the whole projection signal. With an already lower projection prevalence in AO-OCTA, it is expected that PR algorithms applied synergistically with AO-OCTA can yield an even better projection removal. Accurately removing this artifact holds a significant clinical application in better measuring the perfusion density of the ICP and DCP for diabetic retinopathy, retinal vein occlusion and other vascular diseases. It would also improve the specificity and therefore accuracy of CNV detection in advanced AMD. In tandem with AO focusing correction for arbitrary depths, it could also improve the accuracy of capillary density measurement in the choriocapillaris and lamina cribrosa, which are active areas of research. However, a disadvantage of AO-OCTA is that large superficial vessels cast shadows instead of projections, and in situ flow signal becomes irretrievable (e.g. DCP in FIGS. 13 & 14). This is caused by the "shower curtain" effect, in which the influence of scattering on OCT signal attenuation increases with distance from the scatterer. See how ICP in FIGS. 13 and 14 does not show the shadows observed in DCP. Although these shadows are a more prominent in AO-OCTA, they do not account for as many pixels as projection artifacts do in commercial OCTA, and can be excluded with high accuracy by post-processing.

The improved resolution with AO-OCTA may be used for visualizing vascular malformations such as intraretinal microvascular abnormalities (IRMAs), microaneurysms, and dilated capillaries, which are barely recognizable with current commercial OCTA. The presence of IRMAs is one of the features used by the Early Treatment Diabetic Retinopathy Study (ETDRS) to determine severe non-proliferative diabetic retinopathy (NPDR). Diagnosing the severe stage is significant because the risk of progression to proliferative DR within a year is 50%. In neovascular AMD, AO could improve the visualization of CNV with OCTA. CNV often presents in patterns of coralliform complexes or thin capillaries growing from a feeding trunk. It has been hypothesized that proliferation of thin capillary networks (and not large stable arterialized trunks) on OCTA corresponds to the reactivation of vascular endothelial grow factor (VEGF activity) for CNV under anti-VEGF treatment. In principle, AO could help better characterize CNV morphology. Additionally, AO-OCTA could improve the ability to detect mildly reduced flow states where the capillary caliber may be reduced without complete cessation for flow and disappearance of the capillary on OCTA. Finally, AO-OCTA could also assist in imaging polypoidal flow in polypoidal choroidal vasculopathy (PCV). OCT images of PCV are characterized by dome-shaped pigment epithelial detachments (PED) and hyper-reflective spots near the level of the Bruch's membrane, indicative of polypoidal activity. The potential for AO in PCV lies in the promise to improve the discrimination of the decorrelation signal in polyp voxels from background when imaged with OCTA.

Optical Coherence Tomography Angiography Image Processing System

Figure 16:
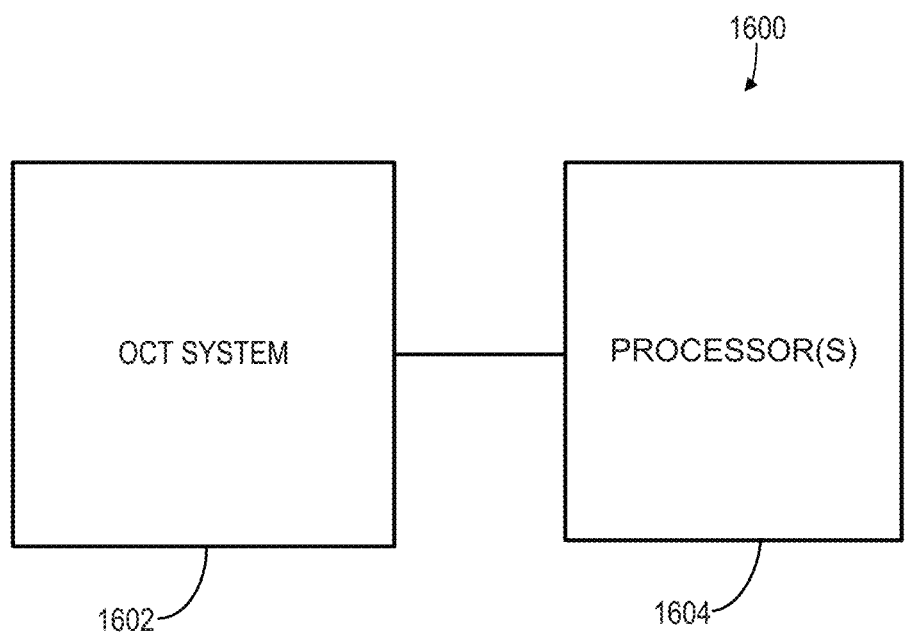
FIG. 16 schematically shows an example system for processing OCT and OCTA datasets in accordance with the disclosure.

FIG. 16 schematically shows an example system 1600 for OCT image processing in accordance with various embodiments. In embodiments, the system 1600 may correspond to one or more of the three OCT systems used in the example systems and/or experiments described above. System 1600 comprises an OCT system 1602 configured to acquire an OCT image comprising OCT interferograms and one or more processors or computing systems 1604 that are configured to implement the various processing routines described herein. OCT system 1600 can comprise an OCT system suitable for structural OCT and OCT angiography applications, e.g., a swept source OCT system or spectral domain OCT system.

In various embodiments, an OCT system can be adapted to allow an operator to perform various tasks. For example, an OCT system can be adapted to allow an operator to configure and/or launch various ones of the herein described methods. In some embodiments, an OCT system can be adapted to generate, or cause to be generated, reports of various information including, for example, reports of the results of scans run on a sample.

In embodiments of OCT systems comprising a display device, data and/or other information can be displayed for an operator. In embodiments, a display device can be adapted to receive an input (e.g., by a touch screen, actuation of an icon, manipulation of an input device such as a joystick or knob, etc.) and the input can, in some cases, be communicated (actively and/or passively) to one or more processors. In various embodiments, data and/or information can be displayed, and an operator can input information in response thereto.

In some embodiments, the above described methods and processes can be tied to a computing system, including one or more computers. In particular, the methods and processes described herein, e.g., the method 100 depicted in FIG. 1, described above, can be implemented as a computer application, computer service, computer API, computer library, and/or other computer program product.

Figure 17:
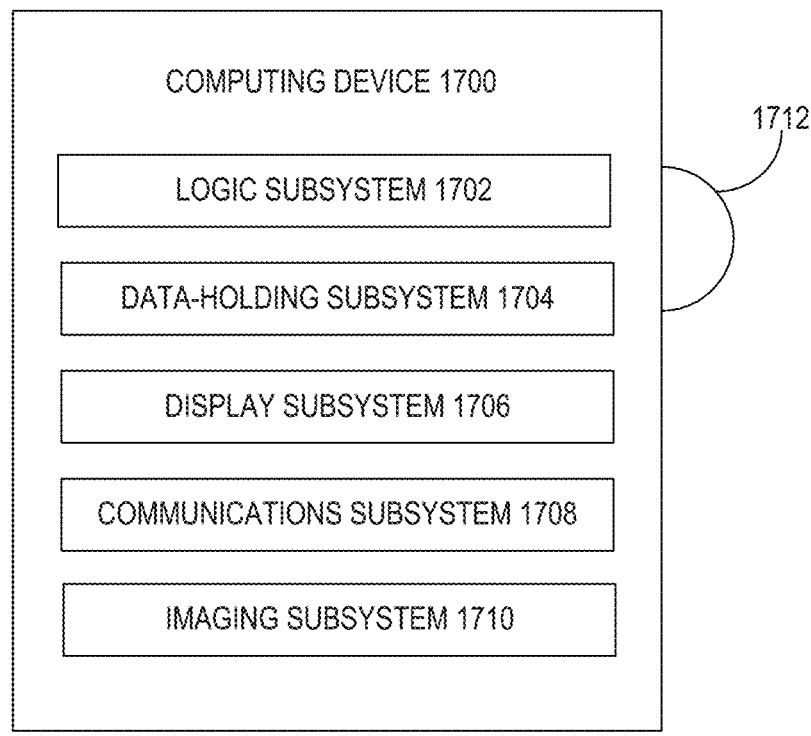
FIG. 17 schematically shows an example of a computing system in accordance with the disclosure.

FIG. 17 schematically shows a non-limiting computing device 1700 that can perform one or more of the above described methods and processes. For example, computing device 1700 can represent a processor included in system 1600 described above, and can be operatively coupled to, in communication with, or included in an OCT system or OCT image acquisition apparatus. Computing device 1700 is shown in simplified form. It is to be understood that virtually any computer architecture can be used without departing from the scope of this disclosure. In different embodiments, computing device 1700 can take the form of a microcomputer, an integrated computer circuit, printed circuit board (PCB), microchip, a mainframe computer, server computer, desktop computer, laptop computer, tablet computer, home entertainment computer, network computing device, mobile computing device, mobile communication device, gaming device, etc.

Computing device 1700 includes a logic subsystem 1702 and a data-holding subsystem 1704. Computing device 1700 can optionally include a display subsystem 1706, a communication subsystem 1708, an imaging subsystem 1710, and/or other components not shown in FIG. 17. Computing device 1700 can also optionally include user input devices such as manually actuated buttons, switches, keyboards, mice, game controllers, cameras, microphones, and/or touch screens, for example.

Logic subsystem 1702 can include one or more physical devices configured to execute one or more machine-readable instructions. For example, the logic subsystem can be configured to execute one or more instructions that are part of one or more applications, services, programs, routines, libraries, objects, components, data structures, or other logical constructs. Such instructions can be implemented to perform a task, implement a data type, transform the state of one or more devices, or otherwise arrive at a desired result.

The logic subsystem can include one or more processors that are configured to execute software instructions. For example, the one or more processors can comprise physical circuitry programmed to perform various acts described herein. Additionally or alternatively, the logic subsystem can include one or more hardware or firmware logic machines configured to execute hardware or firmware instructions. Processors of the logic subsystem can be single core or multicore, and the programs executed thereon can be configured for parallel or distributed processing. The logic subsystem can optionally include individual components that are distributed throughout two or more devices, which can be remotely located and/or configured for coordinated processing. One or more aspects of the logic subsystem can be virtualized and executed by remotely accessible networked computing devices configured in a cloud computing configuration.

Data-holding subsystem 1704 can include one or more physical, non-transitory, devices configured to hold data and/or instructions executable by the logic subsystem to implement the herein described methods and processes. When such methods and processes are implemented, the state of data-holding subsystem 1704 can be transformed (e.g., to hold different data).

Data-holding subsystem 1704 can include removable media and/or built-in devices. Data-holding subsystem 1704 can include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 1704 can include devices with one or more of the following characteristics: volatile, nonvolatile, dynamic, static, read/write, read-only, random access, sequential access, location addressable, file addressable, and content addressable. In some embodiments, logic subsystem 1702 and data-holding subsystem 1704 can be integrated into one or more common devices, such as an application specific integrated circuit or a system on a chip.

FIG. 17 also shows an aspect of the data-holding subsystem in the form of removable computer-readable storage media 1712, which can be used to store and/or transfer data and/or instructions executable to implement the herein described methods and processes. Removable computer-readable storage media 1712 can take the form of CDs, DVDs, HD-DVDs, Blu-Ray Discs, EEPROMs, flash memory cards, USB storage devices, and/or floppy disks, among others.

When included, display subsystem 1706 can be used to present a visual representation of data held by data-holding subsystem 1704. As the herein described methods and processes change the data held by the data-holding subsystem, and thus transform the state of the data-holding subsystem, the state of display subsystem 1706 can likewise be transformed to visually represent changes in the underlying data. Display subsystem 1706 can include one or more display devices utilizing virtually any type of technology. Such display devices can be combined with logic subsystem 1702 and/or data-holding subsystem 1704 in a shared enclosure, or such display devices can be peripheral display devices.

When included, communication subsystem 1708 can be configured to communicatively couple computing device 1700 with one or more other computing devices. Communication subsystem 1708 can include wired and/or wireless communication devices compatible with one or more different communication protocols. As non-limiting examples, the communication subsystem can be configured for communication via a wireless telephone network, a wireless local area network, a wired local area network, a wireless wide area network, a wired wide area network, etc. In some embodiments, the communication subsystem can allow computing device 1700 to send and/or receive messages to and/or from other devices via a network such as the Internet.

When included, imaging subsystem 1710 can be used acquire and/or process any suitable image data from various sensors or imaging devices in communication with computing device 1700. For example, imaging subsystem 1710 can be configured to acquire OCT image data, e.g., interferograms, as part of an OCT system, e.g., OCT system 1602 described above. Imaging subsystem 1710 can be combined with logic subsystem 1702 and/or data-holding subsystem 1704 in a shared enclosure, or such imaging subsystems can comprise periphery imaging devices. Data received from the imaging subsystem can be held by data-holding subsystem 1704 and/or removable computer-readable storage media 1712, for example.

It is to be understood that the configurations and/or approaches described herein are exemplary in nature, and that these specific embodiments or examples are not to be considered in a limiting sense, because numerous variations are possible. The specific routines or methods described herein can represent one or more of any number of processing strategies. As such, various acts illustrated can be performed in the sequence illustrated, in other sequences, in parallel, or in some cases omitted. Likewise, the order of the above-described processes can be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A method of adaptive optics (AO)-optical coherence tomography (OCT), the method comprising:
   receiving OCT data of a sample from an OCT system;
   generating one or more figures of merit based on the OCT data, wherein the one or more figures of merit are volumetric and depth-resolved; and
   adjusting one or more optics parameters of the OCT system to compensate for one or more ocular aberrations based on the one or more figures of merit.

2. The method of claim 1, wherein the one or more ocular aberrations correspond to respective Zernike modes.

3. The method of claim 1, wherein the one or more ocular aberrations is two to ten ocular aberrations.

4. The method of claim 1, wherein the one or more figures of merit are generated during scanning of a sample to obtain the OCT data.

5. The method of claim 1, wherein the generating respective figures of merit of the one or more figures of merit includes determining a maximum value of a merit function among a plurality of iterations with an adaptive step size for a stroke of a deformable mirror, wherein the adaptive step size is adjusted based on a gradient of the merit function.

6. The method of claim 5, wherein the generating the respective figures of merit further includes:
   determining that the gradient of the merit function is negative for a threshold of two or more consecutive iterations of the plurality of iterations; and
   setting a value of the stroke for a next iteration to a first stroke value plus an offset, wherein the first stroke value corresponds to a current maximum value of the merit function.

7. The method of claim 5, wherein the generating the respective figures of merit further includes:
   determining occurrence of a trigger event based on one or more characteristics of the merit function for one or more prior iterations of the plurality of iterations;
   estimating, based on the determination, a first stroke value based on a parabolic fit of the merit function; and
   using the first stroke value for a next iteration of the plurality of iterations.

8. The method of claim 7, wherein the one or more characteristics include that, for a most recent iteration of the prior iterations, the gradient of the merit function is negative and the merit value is greater than a current maximum value of the other prior iterations.

9. The method of claim 1, further comprising:
   estimating a maximum field of view (FOV) for which the OCT data can be compensated for within one or more OCT scans; and
   determining a scanning size for the OCT data based on the maximum FOV.

10. The method of claim 1, wherein the sample is a retina.

11. The method of claim 1, wherein the one or more optics parameters include a stroke of a deformable mirror.

12. The method of claim 11, further comprising:
   obtaining a compensated OCT dataset of the sample based on the determined one or more optics parameters; and
   generating one or more OCT or OCT angiography (OCTA) images based on the compensated OCT dataset.

* * * * *